(12) United States Patent
Swinnen et al.

(10) Patent No.: US 7,998,964 B2
(45) Date of Patent: Aug. 16, 2011

(54) N-HYDROXYAMIDE DERIVATIVES AND USE THEREOF

(75) Inventors: Dominique Swinnen, Beaumont (FR); Jerome Gonzalez, Annemasse (FR)

(73) Assignee: Merck Serono S.A., Coinsins, Vaud (CH)

( * ) Notice: Subject to any disclaimer, the term of this patent is extended or adjusted under 35 U.S.C. 154(b) by 233 days.

(21) Appl. No.: 12/094,921

(22) PCT Filed: Nov. 16, 2006

(86) PCT No.: PCT/EP2006/068574
§ 371 (c)(1),
(2), (4) Date: May 23, 2008

(87) PCT Pub. No.: WO2007/060132
PCT Pub. Date: May 31, 2007

(65) Prior Publication Data
US 2008/0275060 A1    Nov. 6, 2008

Related U.S. Application Data

(60) Provisional application No. 60/740,211, filed on Nov. 28, 2005.

(30) Foreign Application Priority Data

Nov. 24, 2005 (EP) .................................. 05111228

(51) Int. Cl.
*A61K 31/4965* (2006.01)
*C07D 241/04* (2006.01)
*C07D 295/00* (2006.01)

(52) U.S. Cl. .................... 514/255.01; 544/391

(58) Field of Classification Search .............. 514/255.01; 544/391
See application file for complete search history.

(56) References Cited

U.S. PATENT DOCUMENTS 6,908,911 B1 * 6/2005 Hunter et al. ................. 514/183

FOREIGN PATENT DOCUMENTS

| WO | WO 99/39704 | * | 8/1999 |
| WO | WO 01/10834 | * | 2/2001 |
| WO | WO 01/10834 A3 | | 2/2001 |
| WO | WO 01/10835 A1 | | 2/2001 |

OTHER PUBLICATIONS

Clark, et al., Expert Opinion Ther. Targets, 7(1): 19-34 (2003).*
Galis, et al., Circ. Res., 90: 251-262 (2002).*
Leppert, et al., Brain Res. Rev., 36: 249-257 (2001).*
Makrakis, et al., J. of Maternity Fetal & Neonatal Medicine 14(3): 170-176 (2003).*
Skiles, J.W. et al. "The Design, Structure, and Therapeutic Application of Matrix Metalloproteinase Inhibitors" *Current Medicinal Chemistry*, Mar. 2001, pp. 425-474, vol. 8, No. 4.
Wada, C.K. et al. "Phenoxyphenyl Sulfone N-Formylhydroxylamines (Retrohydroxamates) as Potent, Selective, Orally Bioavailable Matrix Metalloproteinase Inhibitors" *Journal of Medicinal Chemistry*, 2002, pp. 219-232, vol. 45.
"MMP-12 Inhibitors" Expert Opinion on Therapeutic Patents, 2004, pp. 1637-1640, vol. 14, No. 11, Ashley Publications.

* cited by examiner

*Primary Examiner* — Noble Jarrell
*Assistant Examiner* — Erich A Leeser
(74) *Attorney, Agent, or Firm* — Saliwanchik, Lloyd & Eisenschenk

(57) ABSTRACT

The present invention is related to N-hydroxyamide derivatives of Formula (I) and use thereof in particular for the treatment and/or prophylaxis of autoimmune disorders, inflammatory diseases, cardiovascular diseases, neurodegenerative diseases, cancer, respiratory diseases and fibrosis, including multiple sclerosis, arthritis, emphysema, chronic obstructive pulmonary disease, liver and pulmonary fibrosis.

19 Claims, No Drawings

N-HYDROXYAMIDE DERIVATIVES AND USE THEREOF

CROSS-REFERENCE TO RELATED APPLICATION

This application is the U.S. national stage application of International Patent Application No. PCT/EP2006/068574, filed Nov. 16, 2006, which claims the benefit of U.S. Provisional Patent Application No. 60/740,211, filed Nov. 28, 2005, the disclosures of which are hereby incorporated by reference in their entireties, including all figures, tables and amino acid or nucleic acid sequences.

FIELD OF THE INVENTION

The present invention is related to N-hydroxyamide derivatives of Formula (I), pharmaceutical composition thereof, methods of preparation thereof and to their use for the treatment and/or prophylaxis of autoimmune disorders and/or inflammatory diseases, cardiovascular diseases, neurodegenerative diseases, cancer, respiratory diseases and fibrosis. Specifically, the present invention is related to N-hydroxyamide derivatives for the modulation, notably the inhibition of the activity or function of matrix metalloproteinases.

BACKGROUND OF THE INVENTION

Metalloproteinases are a superfamily of proteinases (enzymes) named for their dependence on a metal ion (zinc) in the active site.

The matrix metalloproteinases (MMPs) form a metalloproteinase sub-family having as one of major biological function to catalyse the breakdown of connective tissue or extracellular matrix through their ability to hydrolyse various components of the tissue or matrix, such as collagens, gelatins, proteoglycans, fibronectins and elastin.

The matrix metalloproteinase family is further divided according to their function and substrates (Visse al., 2003, *Circ. Res.*, 92: 827-839) and comprises collagenases (MMP-1, MMP-8, MMP-13 and MMP-18), gelatinases (MMP-2 and MMP-9), stromelysins (MMP-3, MMP-10 and MMP-11), membrane-type MMPs (MT-MMP-1 to MT-MMP-6 and MMP-14, MMP-15, MMP-16, MMP-17, MMP-24 and MMP-25), matrilysins (MMP-7 and MMP-26) and other unclassified MMPs such as metalloelastase (MMP-12), enamelysin (MMP-20), epilysin (MMP-28), MMP-19, MMP-22 and MMP-23.

Apart from their role in degrading connective tissue, MMPs are involved in the biosynthesis of TNF-alpha and in the post-translational proteolysis processing, or shedding of biologically important membrane proteins (Hooper et al., 1997, *Biochem J*, 321: 265-279). MMPs for example contribute to the local growth and spread of malignant lesions and therefore have been a target for anti-tumor drug development (Fingleton et al., 2003, *Expert Opin. Ther. Targets*, 7(3):385-397). Disorders such as inflammatory disorders like arthritis (Clark et al., 2003, *Expert. Opin. Ther Targets*, 7(1):19-34), respiratory disorders such as emphysema, arteriosclerosis (Galis et al., 2002, *Circ. Res.*, 90:251-262), neurological disorders such as degenerative nervous system diseases, multiple sclerosis (Leppert et al., 2001, *Brain Res. Rev.*, 36:249-257), periodontitis (Ingman et al., 1996, *J. Clin. Periodontal.*, 23:1127-1132), pre-term labor (Makrakis et al., 2003, *J. Matern Fetal & Neonatal Medicine*, 14(3): 170-6) and wound healing have been demonstrated to be associated with MMPs expression and/or activity.

A wide variety of matrix metalloproteinase inhibitors (MMPIs) has been developed (Skiles et al., 2001, *Current Medicinal Chemistry*, 8, 425-474; Henrotin et al., 2002, *Expert Opin. Ther. Patents*, 12(1):29-43). However, many MMPIs exhibit a muscoskeletal syndrome (tendonitis, fibroplasias, mylasia, arthralasia) as a dose-limiting side effect. It has been proposed that inhibition of MMP-1 or MMP-14 may be responsible for these effects.

Therefore, there is an increasing need to develop matrix metalloproteinase inhibitors with a well-defined specificity profile.

Specific inhibitors, especially towards MMP-1, have been reported, including MMP-13 inhibitors (Skotnicki et al., 2003, *Current Opinion in Drug Discovery and Development*, 6(5):742-759), MMP-12 inhibitors (*Expert. Opin. Ther. Patents*, 2004, 14(11):1637-1640), MMP-2 and MMP-9 inhibitors (Wada et al., 2002, *J. Med. Chem.* 45: 219-232).

The high relevance of the metalloproteinase pathway in some widely spread diseases stresses the need to develop inhibitors, including selective inhibitors of MMPs, especially of MMP-12.

SUMMARY OF THE INVENTION

It is an object of the invention to provide substances which are suitable for the treatment and/or prevention of disorders related to autoimmune disorders and/or inflammatory diseases, cardiovascular diseases, neurodegenerative diseases, stroke, cancer and malignancy, respiratory diseases, metabolic diseases, allergic and dermatologic diseases, pre-term labor, endometriosis and fibrosis.

It is further an object of the present invention to provide substances which are suitable for the treatment and/or prevention of multiple sclerosis, arthritis such as osteoarthritis and rheumatoid arthritis, emphysema, psoriasis, obstructive pulmonary disease and fibrosis.

It is notably an object of the present invention to provide chemical compounds which are able to modulate, especially inhibit the activity or function of matrix metalloproteinases, especially gelatinases and elastase in mammals, especially in humans.

It is furthermore an object of the present invention to provide a new category of pharmaceutical formulations for the treatment of and/or diseases mediated selected from autoimmune disorders and/or inflammatory diseases, cardiovascular diseases, neurodegenerative diseases, stroke, cancer and malignancy, respiratory diseases, metabolic diseases, allergic and dermatologic diseases, pre-term labor, endometriosis and fibrosis.

It is furthermore an object of the present invention to provide processes for making chemical compounds according to the invention.

It is finally an object of the present invention to provide a method for the treatment and/or prevention of disorders selected from autoimmune disorders and/or inflammatory diseases, cardiovascular diseases, neurodegenerative diseases, stroke, cancer and malignancy, respiratory diseases, metabolic diseases, allergic and dermatologic diseases, pre-term labor, endometriosis and fibrosis.

In a first aspect, the invention provides N-hydroxyamide derivatives of Formula (I):

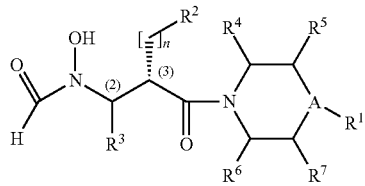

wherein A, $R^1$, $R^2$, $R^3$, $R^4$, $R^5$, $R^6$, $R^7$ and n are defined in the detailed description.

In a second aspect, the invention provides a compound according to Formula (I) for use as a medicament.

In a third aspect, the invention provides a use of a compound according to Formula (I) for the preparation of a pharmaceutical composition for the treatment of a disorder selected from autoimmune disorders and/or inflammatory diseases, cardiovascular diseases, neurodegenerative diseases, stroke, cancer and malignancy, respiratory diseases, metabolic diseases, allergic and dermatologic diseases, preterm labor, endometriosis and fibrosis.

In a fourth aspect, the invention provides a pharmaceutical composition comprising at least one a compound according to Formula (I) and a pharmaceutically acceptable carrier, diluent or excipient thereof.

In a fifth aspect, the invention provides a method of treatment comprising the administration of a compound according to Formula (I) in a patient in need thereof.

In a sixth aspect, the invention provides methods of synthesis of a compound according to Formula (I).

In a seventh aspect, the invention provides compounds according to Formula (II):

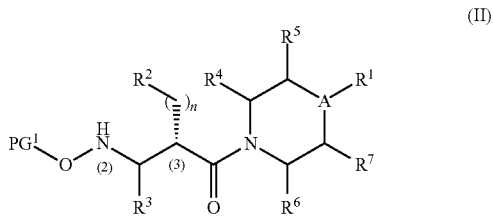

wherein $R^1$, $R^2$, $R^3$, $R^4$, $R^5$, $R^6$, $R^7$ and n are defined as above and $PG^1$ is H or a protecting group such as benzyl, t-butyl, THP, TMS, TBS:

DETAILED DESCRIPTION OF THE INVENTION

The following paragraphs provide definitions of the various chemical moieties that make up the compounds according to the invention and are intended to apply uniformly through-out the specification and claims unless an otherwise expressly set out definition provides a broader definition.

The term "MMPS" refers to "matrix metalloproteinases". For recent reviews of MMPs, see Visse et al., 2003 above; Fingleton et al., 2003, above; Clark et al., 2003, above and Doherty et al., 2002, *Expert Opinion Therapeutic Patents* 12(5):665-707.

Illustrative but not limiting examples of such MMPs are:
Collagenases: usually associated with diseases linked to breakdown of collagen-based tissue e.g. rheumatoid arthritis and osteoarthritis:

MMP-1 (also known as collagenase 1, or fibroblast collagenase), substrates collagen I, collagen II, collagen III, gelatin, proteoglycans. Over-expression of this enzyme is believed to be associated with emphysema, with hyperkeratosis and atherosclerosis, overexpressed alone in papillary carcinoma.

MMP-8 (also known as collagenase 2, or neutrophil collagenase), substrates collagen I, collagen II, collagen III, collagen V, collagen VII, collagen IX, gelatin over-expression of which can lead to non-healing chronic ulcers.

MMP-13 (also known as collagenase 3), substrates collagen I, collagen II, collagen III, collagen IV, collagen IX, collagen X, collagen XIV, fibronectin, gelatin, recently identified as being over-expressed alone in breast carcinoma and involved in rheumatoid arthritis.

Stromelysins:
MMP-3 (also known as stromelysin 1), substrates collagen III, collagen IV, collagen V, collagen IX, collagen X, laminin, nidogen, over-expression believed to be involved in atherosclerosis, aneurysm and restenosis.

Gelatinases—inhibition believed to exert a favorable effect on cancer, in particular invasion and metastasis.

MMP-2 (also known as gelatinase A, 72 kDa gelatinase, basement membrane collagenase, or proteoglycanase), substrates Collagen I, Collagen II, Collagen IV, Collagen V, Collagen VII, Collagen X, Collagen XI, collagen XIV, elastin, fibronectin, gelatin, nidogen, believed to be associated with tumor progression through specificity for type IV Collagen (high expression observed in solid tumors and believed to be associated with their ability to grow, invade, develop new blood vessels and metastasize) and to be involved in acute lung inflammation and in respiratory distress syndrome (Krishna et al., 2004, *Expert Opin. Invest. Drugs*, 13(3): 255-267).

MMP-9 (also known as gelatinase B, or 92 kDa gelatinase), substrates Collagen I, Collagen III, Collagen IV, Collagen V, Collagen VII, collagen X, Collagen XIV, elastin, fibronectin, gelatin, nidogen. The above enzyme is believed to be associated with tumor progression through specificity for type IV Collagen, to be released by eosinophils in response to exogenous factors such as air pollutants, allergens and viruses, to be involved in the inflammatory response in multiple sclerosis (Opdenakker et al., 2003, *The Lancet Neurology*, 2, 747-756) and asthma and to be involved in acute lung inflammation, respiratory distress syndrome, chronic obstructive pulmonary disorder (COPD) and/or asthma (Krishna et al., 2004, above). MMP-9 is also thought to be involved in stroke (Horstmann et al., 2003, *Stroke*, 34(9): 2165-70).

Unclassified MMPs:
MMP-12 (also known as metalloelastase, human macrophage elastase, or HME), substrates fibronectin, laminin, believed to play a role in tumour growth inhibition and regulation of inflammation such as multiple sclerosis (Vos et al., 2003, *Journal of Neuroimmunology*, 138, 106-114) and to play a pathological role in emphysema, COPD (Belvisi et al., 2003, *Inflamm. Res.* 52: 95-100) and in atherosclerosis, aneurysm and restenosis.

The expression "MMP-associated disorder" refers to a disorder which is treatable according to the invention and that encompasses all disorders in which the expression and/or activity of at least one MMP needs to be decreased irrespective of the cause of such disorders. Such disorders include, for example, those caused by inappropriate extracellular matrix (ECM) degradation.

Illustrative but not limiting examples of such MMP-associated disorders are:

Cancer such as breast cancer and solid tumors; inflammatory disorders such as for example inflammatory bowel diseases and neuroinflammation such as multiple sclerosis; lung diseases such as chronic obstructive pulmonary disorder (COPD), emphysema, asthma, acute lung injury, and acute respiratory distress syndrome; dental diseases such as periodontal disease and gingivitis; joint and bone diseases such as osteoarthritis and rheumatoid arthritis; liver diseases such as liver fibrosis, cirrhosis and chronic liver disease; fibrotic diseases such as pulmonary fibrosis, pancreatitis, lupus, glomerulosclerosis, systemic sclerosis skin fibrosis, post-radiation fibrosis and cystic fibrosis; vascular pathologies such as aortic aneurysm, atherosclerosis, hypertension, cardiomyopathy and myocardial infarction; restenosis; ophthalmological disorders such as diabetic retinopathy, dry eye syndrome, macula degeneration and corneal ulceration and degenerative diseases of the central nervous system such as amyotrophic lateral sclerosis.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_8$-alkyl" refers to monovalent alkyl groups having 1 to 5 carbon atoms.

"Heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Aryl include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro] benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 1,2,3,4-tetrahydroquinolyl, 1,2,3,4-tetrahydroisoquinolyl, purinyl, pteridinyl, carbazolyl, xanthenyl or benzoquinolyl.

"$C_1$-$C_6$-alkyl heteroaryl" refers to heteroaryl groups having a $C_1$-$C_6$-alkyl substituent, including methyl furyl and the like.

"Heteroaryl $C_1$-$C_6$-alkyl" refers to $C_1$-$C_6$-alkyl groups having a heteroaryl substituent, including furyl methyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkenyl aryl" refers to an aryl groups having a $C_2$-$C_6$-alkenyl substituent, including vinyl phenyl and the like.

"Aryl $C_2$-$C_6$-alkenyl" refers to a $C_2$-$C_6$-alkenyl groups having an aryl substituent, including phenyl vinyl and the like.

"$C_2$-$C_6$-alkenyl heteroaryl" refers to heteroaryl groups having a $C_2$-$C_6$-alkenyl substituent, including vinyl pyridinyl and the like.

"Heteroaryl $C_2$-$C_6$-alkenyl" refers to $C_2$-$C_6$-alkenyl groups having a Heteroaryl substituent, including pyridinyl vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl), $C_3$-$C_8$-cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidine, piperidine, piperazine, morpholine, tetrahydrofurane and the like.

"$C_1$-$C_6$-alkyl cycloalkyl" refers to $C_3$-$C_8$-cycloalkyl groups having a $C_1$-$C_6$-alkyl substituent, including methyl cyclopentyl and the like.

"Cycloalkyl $C_1$-$C_6$-alkyl" refers to $C_1$-$C_6$-alkyl groups having a $C_3$-$C_8$-cycloalkyl substituent, including 3-cyclopentyl propyl and the like.

"$C_1$-$C_6$-alkyl heterocycloalkyl" refers to heterocycloalkyl groups having a $C_1$-$C_6$-alkyl substituent, including 1-methylpiperazine and the like.

"Heterocycloalkyl $C_1$-$C_6$-alkyl" refers to $C_1$-$C_6$-alkyl groups having a heterocycloalkyl substituent, including 4-methyl piperidyl and the like.

"Carboxy" refers to the group —C(O)OH.

"Carboxy $C_1$-$C_6$-alkyl" refers to $C_1$-$C_6$-alkyl groups having an carboxy substituent, including 2-carboxyethyl and the like.

"Acyl" refers to the group —C(O)R where R includes "$C_1$-$C_{12}$-alkyl", preferably "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyl $C_1$-$C_6$-alkyl" to $C_1$-$C_6$-alkyl groups having an acyl substituent, including acetyl, 2-acetylethyl and the like.

"Acyl aryl" refers to aryl groups having an acyl substituent, including 2-acetylphenyl and the like.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acyloxy $C_1$-$C_6$-alkyl" refers to $C_1$-$C_6$-alkyl groups having an acyloxy substituent, including propionic acid ethyl ester and the like.

"Alkoxy" refers to the group —O—R where R includes "$C_1$-$C_6$-alkyl" or "aryl" or "hetero-aryl" or "aryl $C_1$-$C_6$-alkyl" or "heteroaryl $C_1$-$C_6$-alkyl". Preferred alkoxy groups include for example, methoxy, ethoxy, phenoxy and the like.

"Alkoxy $C_1$-$C_6$-alkyl" refers to alkoxy groups having a $C_1$-$C_6$-alkyl substituent, including methoxy, methoxyethyl and the like.

"Alkoxycarbonyl" refers to the group —C(O)OR where R includes H, "$C_1$-$C_6$-alkyl" or "aryl" or "heteroaryl" or "aryl $C_1$-$C_6$-alkyl" or "heteroaryl $C_1$-$C_6$-alkyl" or "heteroalkyl".

"Alkoxycarbonyl $C_1$-$C_6$-alkyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "aryl $C_1$-$C_6$-alkyl" or "heteroaryl $C_1$-$C_6$-alkyl", including N-phenyl formamide.

"Aminocarbonyl $C_1$-$C_6$-alkyl" refers to $C_1$-$C_6$-alkyl groups having an aminocarbonyl substituent, including 2-(dimethylaminocarbonyl)ethyl, N-ethyl acetamide, N,N-Diethyl-acetamide and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Acylamino $C_1$-$C_6$-alkyl" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl", and where R' and R", together with the nitrogen atom to which they are attached, can optionally form a 3-8-membered heterocycloalkyl ring.

"Ureido $C_1$-$C_6$-alkyl" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Amino" refers to the group —NRR' where each R,R' is independently hydrogen or "C$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Amino $C_1$-$C_6$-alkyl" refers to $C_1$-$C_6$-alkyl groups having an amino substituent, including 2-(1-pyrrolidinyl)ethyl and the like.

"Ammonium" refers to a positively charged group —N$^+$RR'R", where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"Ammonium $C_1$-$C_6$-alkyl" refers to $C_1$-$C_6$-alkyl groups having an ammonium substituent, including 1-ethylpyrrolidinium and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyloxy $C_1$-$C_6$-alkyl" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonyl $C_1$-$C_6$-alkyl" refers to $C_1$-$C_5$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfinyl $C_1$-$C_6$-alkyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., a —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "alkynylheteroaryl $C_2$-$C_6$", "cycloalkyl $C_1$-$C_6$-alkyl", "heterocycloalkyl $C_1$-$C_6$-alkyl". Preferred sulfanyl groups include methylsulfanyl, ethylsulfanyl, and the like.

"Sulfanyl $C_1$-$C_6$-alkyl" refers to $C_1$-$C_6$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Sulfonylamino $C_1$-$C_6$-alkyl" refers to $C_1$-$C_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Aminosulfonyl $C_1$-$C_6$-alkyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkenyl", "alkynyl", "aryl", "heteroaryl", "cycloalkyl", "heterocycloalkyl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "aryl $C_1$-$C_6$-alkyl", "heteroaryl $C_1$-$C_6$-alkyl", "cycloalkyl $C_1$-$C_6$-alkyl", "heterocycloalkyl $C_1$-$C_6$-alkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like.

"Pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, methane sulfonic acid, naphthalene disulfonic acid, and poly-galacturonic acid, as well as salts formed with basic amino acids such as Lysine or Arginine.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group. For example, a chemical masking group for alcohol derivatives could be selected from carboxylic acid ester (e.g. acetate, lysine ester) or phosphoric acid esters (e.g. phosphoric acid monoester).

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. IFN-β suitable in accordance with the present invention is commercially available e.g. as REBIF (Serono), AVONEX (Biogen) or BETAFERON (Schering).

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably, IFN-beta is intended to mean recombinant Interferon beta-1a.

IFN-β suitable in accordance with the present invention is commercially available e.g. as REBIF (Serono), AVONEX (Biogen) or BETAFERON (Schering). The use of interferons of human origin is also preferred in accordance with the present invention. The term interferon, as used herein, is intended to encompass salts, functional derivatives, variants, analogs and active fragments thereof.

REBIF (recombinant interferon-β) is the latest development in interferon therapy for multiple sclerosis (MS) and represents a significant advance in treatment. REBIF is interferon (IFN)-beta 1a, produced from mammalian cell lines. It was established that interferon beta-1a given subcutaneously three times per week is efficacious in the treatment of Relapsing-Remitting Multiple Sclerosis (RRMS). Interferon beta-1a can have a positive effect on the long-term course of MS by reducing number and severity of relapses and reducing the burden of the disease and disease activity as measured by MRI. The dosing of IFN-β in the treatment of relapsing-remitting MS according to the invention depends on the type of IFN-β used.

In accordance with the present invention, where IFN is recombinant IFN-β1b produced in *E. Coli*, commercially available under the trademark BETASERON, it may preferably be administered subcutaneously every second day at a dosage of about of 250 to 300 μg or 8 MIU to 9.6 MIU per person.

In accordance with the present invention, where IFN is recombinant IFN-β1a, produced in Chinese Hamster Ovary cells (CHO cells), commercially available under the trademark AVONEX, it may preferably be administered intramuscularly once a week at a dosage of about of 30 μg to 33 μg or 6 MIU to 6.6 MIU per person.

In accordance with the present invention, when IFN is recombinant IFN-β1a, produced in Chinese Hamster Ovary cells (CHO cells), commercially available under the trademark REBIF, it may preferably be administered subcutaneously three times a week (TIW) at a dosage of 22 to 44 μg or 6 MIU to 12 MIU per person.

Compounds according to the present invention also comprise pharmaceutically acceptable salts thereof. Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

It has been found that compounds of the present invention are modulators of the matrix metalloproteinases, including MMP-12. When the matrix metalloproteinase enzyme is inhibited by the compounds of the present invention, the inhibited MMP(s) is (are) unable to exert its enzymatic, biological and/or pharmacological effects.

The compounds of the present invention are therefore useful in the treatment and prevention of autoimmune disorders and/or inflammatory diseases, cardiovascular diseases, neurodegenerative diseases, stroke, cancer and malignancy, respiratory diseases, metabolic diseases, allergic and dermatologic diseases, pre-term labor, endometriosis and fibrosis.

In one embodiment, the invention provides derivatives of Formula (I)

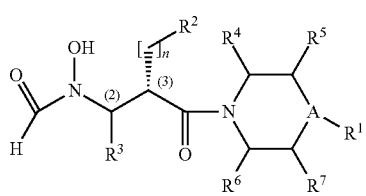

A is selected from —C(B)— and N;

B is H or B forms a bond with either $R^5$ or $R^7$;

$R^1$ is selected from H; optionally substituted $C_1$-$C_6$ alkyl; optionally substituted $C_2$-$C_6$ alkenyl; optionally substituted $C_2$-$C_6$ alkynyl; optionally substituted $C_3$-$C_8$-cycloalkyl, including cyclohexyl; optionally substituted heterocycloalkyl; optionally substituted aryl, including optionally substituted phenyl such as phenyl, halophenyl such as fluorophenyl (e.g. 2-fluorophenyl, 4-fluorophenyl, 3-chlorophenyl), chlorophenyl (e.g. 2-chlorophenyl, 4-chlorophenyl), chloro-2-fluorophenyl and 2-fluoro-5-methoxyphenyl, cycloalkyl phenyl (e.g. 4-cyclohexylphenyl), alkyl phenyl (e.g. 4-propylphenyl, 4-tert-butylphenyl, 4-methyl phenyl), alkoxy phenyl such as methoxy phenyl (e.g. 4-methoxyphenyl, 3,4-dimethoxyphenyl, 3-methoxyphenyl, 3-fluoro-4-methoxy phenyl. 3-fluoro-4-(trifluoromethoxy)phenyl), butoxy phenyl (e.g. 4-tert-butoxyphenyl), propoxy phenyl (e.g. 4-isopropoxyphenyl, 3-fluoro-4-isopropoxy phenyl) and ethoxy phenyl (e.g. 4-ethoxyphenyl, 4-propoxy phenyl, 2,2,2-trifluoroethoxyphenyl), cyanophenyl (e.g. 2-cyanophenyl), trifluoromethyl phenyl (e.g. 4-trifluoromethyl phenyl), trifluoromethoxy phenyl (4-trifluoromethoxy)phenyl), sulfonyl phenyl (e.g. 4-(methylsulfonyl)phenyl, 4-(trifluoromethyl sulfonyl)), amino phenyl (e.g. 4-(dimethylamino)phenyl), biphenyl (e.g. 4-biphenyl, methoxy biphenyl, 4-fluorobiphenyl-4-yl, 4-methoxy biphenyl-4-yl, 4-bromobiphenyl-4-yl), oxazolyl phenyl (e.g. 1,3-oxazol-5-yl)phenyl and benzofuranyl phenyl (e.g. 1-benzofuran-3-yl)phenyl; optionally substituted heteroaryl, including optionally substituted pyridinyl, such as pyridinyl, methylpyridinyl (e.g. 4-methylpyridin-2-yl, 6-methylpyridin-2-yl), halo pyridinyl such as chloro pyridinyl (e.g. 6-chloropyridin-2-yl, 5-chloropyridin-2-yl, 3,5-dichloropyridin-4-yl) and bromo pyridinyl (5-bromopyridin-2-yl), trifluoromethylpyridinyl (e.g. 3-(trifluoromethyl)pyridin-2-yl, 4-(trifluoromethyl)pyridin-2-yl, 5-(trifluoromethyl)pyridin-2-yl), cyano pyridinyl (e.g. 5-cyanopyridin-2-yl), phenyl pyridinyl (e.g. 5-phenyl pyridin-2-yl) and optionally substituted fused pyridinyl (e.g. 4-[6-methyl-2-(trifluoromethyl)quinolin-4-yl], 4-quinolin-3-yl, 4-quinolin-5-yl); including optionally substituted pyrazinyl (e.g. 4-pyrazin-2-yl); including optionally substituted thiadiazolyl such as such as 3-phenyl thiadiazolyl (e.g. 3-phenyl-1,2,4-thiadiazolyl-5-yl); including optionally substituted pyrimidinyl (e.g. 4-pyrimidinyl-2-yl, 5-fluoropyrimidin-2-yl); including optionally substituted oxadiazolyl such as 5-phenyl-1,2,4-oxadiazol-3-yl, 4-pyridin-4-yl-1,2,4-oxadiazol-3-yl, 5-(2-thienyl)-1,2,4-oxadiazol-3-yl and 5-(4-fluorophenyl)-1,3,4-oxadiazol-2-yl; including optionally substituted benzofuranyl (e.g. 1-benzofuran-5-yl); including optionally substituted thienyl (e.g. 5-chloro-2-thienyl) and including optionally substituted benzodioxolyl (e.g. 1,3-benzodioxol-5-yl, 2,2-difluoro-1,3-benzodioxol-5-yl); optionally substituted $C_3$-$C_8$-cycloalkyl $C_1$-$C_6$ alkyl; optionally substituted heterocycloalkyl $C_1$-$C_6$ alkyl, including 2-morpholin-4-ylethyl; optionally substituted heteroaryl $C_1$-$C_6$ alkyl, including 2-thienyl ethyl; optionally substituted amino, including optionally substituted phenyl amino (e.g. phenyl amino, 3-methoxyphenyl amino, 3-(dimethylamino)phenyl amino, 4-ethoxyphenyl amino), heteroaryl amino (e.g. 4-trifluoromethyl)pyrimidin-2-yl, 3-aminopyridin-2-yl) and optionally substituted alkoxy, including 4-(pyridin-2-yloxy), 4-(trifluoromethyl) phenoxy and 2-chlorophenoxy;

$R^2$ is selected from H; optionally substituted $C_1$-$C_6$ alkyl, including isopropyl; optionally substituted $C_2$-$C_6$ alkenyl; optionally substituted $C_2$-$C_6$ alkynyl; optionally substituted $C_3$-$C_8$-cycloalkyl, including cyclopentyl; optionally substituted heterocycloalkyl; optionally substituted alkoxy such as phenyl-methylene-oxy; optionally substituted aryl, including optionally substituted phenyl such as phenyl, ethoxy phenyl or trifluoromethoxy phenyl and optionally substituted heteroaryl;

$R^3$ is selected from H, optionally substituted $C_1$-$C_6$ alkyl, optionally substituted $C_2$-$C_6$ alkenyl and optionally substituted $C_2$-$C_6$ alkynyl;

$R^4$, $R^5$, $R^6$ and $R^7$ are independently selected from H; optionally substituted $C_1$-$C_6$ alkyl, including methyl; optionally substituted $C_2$-$C_6$ alkenyl; optionally substituted $C_2$-$C_6$ alkynyl; or $R^4$ and $R^7$ can form together a —$CH_2$— linkage for example to form with the piperazine ring a 2,5-diazabicyclo[2.2.1]hept-2-yl ring;

n is an integer selected from 1, 2, 3, 4, 5 and 6;

Carbons (2) and (3) are two chiral centers, wherein chiral center (2) has a configuration selected from "S" and "R" and wherein chiral center (3) has a "S" configuration.

The "S" configuration of chiral center (3) is such that the carbon bearing $R^2$ is assumed to have the lowest priority among the carbons in the Cahn-Ingold-Prelog chirality rule (see Eliel et al., 1994, in "*Stereochemistry of Organic compounds*", Wiley Interscience). Further chiral centers may be present in compounds according to Formula (I) and the invention intends to encompass as well optically active forms as enantiomers, diastereomers and its racemate forms, as well as pharmaceutically acceptable salts thereof of compounds according to Formula (I), the configuration of chiral center (3) being "S".

In a preferred embodiment, the invention Formula (I) having the following Formula Ia:

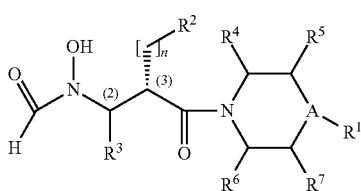

(Ia)

wherein A is selected from —CH and N; $R^1$, $R^2$, $R^3$, $R^4$, $R^5$, $R^6$, $R^7$ and n are defined in the detailed description.

In another preferred embodiment, the invention Formula (I) having the following Formula Ib:

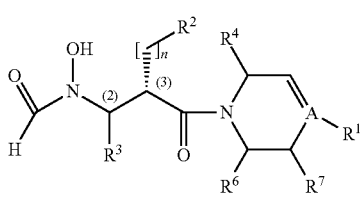

(Ib)

wherein A is a carbon atom and $R^1$, $R^2$, $R^3$, $R^4$, $R^6$, $R^7$ and n are defined in the detailed description.

In another preferred embodiment, the invention provides derivatives of Formula (I) wherein $R^1$ is selected from optionally substituted aryl and optionally substituted heteroaryl.

In another preferred embodiment, the invention provides derivatives of Formula (I) wherein $R^2$ is selected from H, optionally substituted $C_1$-$C_6$ alkyl, optionally substituted $C_2$-$C_6$ alkenyl and optionally substituted $C_2$-$C_6$ alkynyl.

In another preferred embodiment, the invention provides derivatives of Formula (I) wherein $R^2$ is selected from optionally substituted $C_3$-$C_8$-cycloalkyl, including cyclopentyl and optionally substituted heterocycloalkyl.

In another preferred embodiment, the invention provides derivatives of Formula (I) wherein $R^2$ is optionally substituted alkoxy, such as phenyl-methylen-oxy.

In another preferred embodiment, the invention provides derivatives of Formula (I) wherein $R^2$ is aryl such as optionally substituted phenyl.

In another preferred embodiment, the invention provides derivatives of Formula (I) wherein $R^3$ is H.

In another preferred embodiment, the invention provides derivatives of Formula (I) wherein $R^4$, $R^5$ and $R^7$ are H.

In another preferred embodiment, the invention provides derivatives of Formula (I) wherein $R^6$ is selected from H and optionally substituted $C_1$-$C_6$ alkyl, including methyl.

In a further embodiment, the invention provides derivatives of Formula (I) wherein $R^6$ is H.

In a further embodiment, the invention provides derivatives of Formula (I) wherein $R^6$ is methyl.

In another preferred embodiment, the invention provides derivatives of Formula (I) wherein $R^4$ and $R^7$ can form together a —$CH_2$— linkage for example to form with the piperazine ring a 2,5-diazabicyclo[2.2.1]hept-2-yl ring.

In another preferred embodiment, the invention provides derivatives of Formula (I) wherein A is N.

In another preferred embodiment, the invention provides derivatives of Formula (I) wherein A is —CH.

In another preferred embodiment, the invention provides derivatives of Formula (I) wherein $R^1$ is selected from optionally substituted aryl, including optionally substituted phenyl such as phenyl, fluorophenyl chlorophenyl, methoxy phenyl, ethoxy phenyl, cyanophenyl, trifluoromethyl phenyl, trifluoromethoxy phenyl, biphenyl, 4-chloro-2-fluorophenyl, 2-fluoro-5-methoxyphenyl, alkyl phenyl, methoxy phenyl, butoxy phenyl, propoxy phenyl, ethoxy phenyl, sulfonyl phenyl, amino phenyl, oxazolyl phenyl and benzofuran phenyl; optionally substituted heteroaryl, including optionally substituted pyridinyl, such as pyridinyl, methylpyridinyl, chloro pyridinyl, trifluoromethylpyridinyl, cyano pyridinyl, phenyl pyridinyl and optionally substituted fused pyridinyl; including optionally substituted pyrazinyl; including optionally substituted thiadiazolyl such as such as 3-phenyl thiadiazolyl; including optionally substituted pyrimidinyl; including optionally substituted oxadiazolyl; including optionally substituted quinolinyl; including optionally substituted thienyl; including optionally substituted benzofuranyl; including optionally substituted benzodioxolyl;

$R^2$ is selected from H; optionally substituted $C_1$-$C_6$ alkyl, including isopropyl; optionally substituted $C_2$-$C_6$ alkenyl, optionally substituted $C_2$-$C_6$ alkynyl and optionally substituted alkoxy including phenyl-methylene-oxy;

$R^3$, $R^4$, $R^5$ and $R^7$ are H; $R^6$ is selected from H and methyl; A is N; and n is an integer selected from 1, 2, 3, 4, 5 and 6, preferably selected from 1, 2 and 3.

In another preferred embodiment, the invention provides derivatives of Formula (I) wherein $R^1$ is selected from optionally substituted aryl, including optionally substituted phenyl such as phenyl, fluorophenyl chlorophenyl, methoxy phenyl, ethoxy phenyl, cyanophenyl, trifluoromethyl phenyl, trifluoromethoxy phenyl, biphenyl and 4-chloro-2-fluorophenyl, 2-fluoro-5-methoxyphenyl, alkyl phenyl, methoxy phenyl, butoxy phenyl, propoxy phenyl, ethoxy phenyl, sulfonyl phenyl, amino phenyl, oxazolyl phenyl and benzofuran phenyl; optionally substituted heteroaryl, including optionally substituted pyridinyl, such as pyridinyl, methylpyridinyl, chloro pyridinyl, trifluoromethylpyridinyl, cyano pyridinyl, phenyl pyridinyl and optionally substituted fused pyridinyl; including optionally substituted pyrazinyl; including optionally substituted thiadiazolyl such as such as 3-phenyl thiadiazolyl; including optionally substituted pyrimidinyl; including optionally substituted oxadiazolyl; including optionally substituted quinolinyl; including optionally substituted thienyl; including substituted benzofuranyl; including optionally substituted benzodioxolyl;

$R^2$ is selected from H; optionally substituted $C_1$-$C_6$ alkyl, including isopropyl; optionally substituted $C_2$-$C_6$ alkenyl, optionally substituted $C_2$-$C_6$ alkynyl and optionally substituted alkoxy including phenyl-methylene-oxy;

$R^3$, $R^4$, $R^5$ and $R^7$ are H; $R^6$ is selected from H and methyl; A is —CH; and n is an integer selected from 1, 2, 3, 4, 5 and 6, preferably selected from 1, 2 and 3.

In another preferred embodiment, the invention provides derivatives of Formula (I) wherein $R^1$ is selected from optionally substituted aryl, including optionally substituted phenyl such as phenyl, fluorophenyl chlorophenyl, methoxy phenyl, ethoxy phenyl, cyanophenyl, trifluoromethyl phenyl, trifluoromethoxy phenyl, biphenyl and 4-chloro-2-fluorophenyl, 2-fluoro-5-methoxyphenyl, alkyl phenyl, methoxy phenyl, butoxy phenyl, propoxy phenyl, ethoxy phenyl, sulfonyl phenyl, amino phenyl, oxazolyl phenyl and benzofuran phenyl; optionally substituted heteroaryl, including optionally substituted pyridinyl, such as pyridinyl, methylpyridinyl, chloro pyridinyl, trifluoromethylpyridinyl, cyano pyridinyl, phenyl pyridinyl and optionally substituted fused pyridinyl; including optionally substituted pyrazinyl; including optionally substituted thiadiazolyl such as such as 3-phenyl thiadiazolyl; including optionally substituted pyrimidinyl; including optionally substituted oxadiazolyl; including optionally substituted quinolinyl; including optionally substituted thienyl; substituted benzofuranyl; including optionally substituted benzodioxolyl;

$R^2$ is selected from H; optionally substituted $C_1$-$C_6$ alkyl, including isopropyl; optionally substituted $C_2$-$C_6$ alkenyl, optionally substituted $C_2$-$C_6$ alkynyl and optionally substituted alkoxy including phenyl-methylene-oxy;

$R^3$ and $R^5$ are H; $R^6$ is selected from H and methyl; $R^4$ and $R^7$ can form together a —$CH_2$-linkage; A is N; and n is an integer selected from 1, 2, 3, 4, 5 and 6, preferably selected from 1, 2 and 3.

In another preferred embodiment, the invention provides derivatives of Formula (Ib) wherein $R^1$ is selected from optionally substituted aryl, including optionally substituted phenyl such as phenyl, fluorophenyl chlorophenyl, methoxy phenyl, ethoxy phenyl, cyanophenyl, trifluoromethyl phenyl, trifluoromethoxy phenyl, biphenyl and 4-chloro-2-fluorophenyl, 2-fluoro-5-methoxyphenyl; alkyl phenyl, methoxy phenyl, butoxy phenyl, propoxy phenyl, ethoxy phenyl, sulfonyl phenyl, amino phenyl, oxazolyl phenyl and benzofuran phenyl (e.g. 1-benzofuran-3-yl)phenyl; optionally substituted heteroaryl; optionally substituted heteroaryl, including optionally substituted pyridinyl, such as pyridinyl, methylpyridinyl, chloro pyridinyl, trifluoromethylpyridinyl, cyano pyridinyl, phenyl pyridinyl and optionally substituted fused pyridinyl; including optionally substituted pyrazinyl; including optionally substituted thiadiazolyl such as such as 3-phenyl thiadiazolyl; including optionally substituted pyrimidinyl; including optionally substituted oxadiazolyl; including optionally substituted quinolinyl; including optionally substituted thienyl; including optionally substituted benzofuranyl; including optionally substituted benzodioxolyl;

$R^2$ is selected from H; optionally substituted $C_1$-$C_6$ alkyl, including isopropyl; optionally substituted $C_2$-$C_6$ alkenyl, optionally substituted $C_2$-$C_6$ alkynyl, optionally substituted aryl, optionally substituted heteroaryl and optionally substituted alkoxy including phenyl-methylene-oxy;

$R^3$, $R^4$ and $R^6$ are H;

n is an integer selected from 1, 2, 3, 4, 5 and 6, preferably selected from 1, 2 and 3.

Compounds of the present invention include in particular those selected from the following group:

hydroxy((2S)-2-{[4-(4-methoxyphenyl)piperazin-1-yl]carbonyl}-4-methylpentyl) formamide;

{(2S)-2-[(4-biphenyl-4-ylpiperazin-1-yl)carbonyl]-4-methylpentyl}hydroxyformamide.

In another embodiment of the invention, are provided N-hydroxyamide derivatives according to Formula (I) for use as a medicament.

In another embodiment of the invention, is provided a pharmaceutical composition comprising at least one N-hydroxyamide derivative according to the invention and a pharmaceutically acceptable carrier, diluent or excipient thereof.

In another embodiment of the invention, is provided a use of N-hydroxyamide derivatives according to Formula (I) for the preparation of a medicament for the prophylaxis and/or treatment of a disorder selected from autoimmune disorders, inflammatory diseases, stroke, cardiovascular diseases, neurodegenerative diseases, cancer and malignancy, metabolic diseases, allergic and dermatologic diseases, respiratory diseases and fibrosis, including multiple sclerosis, inflammatory bowel disease, arthritis, psoriasis, asthma, emphysema, pre-term labor, endometriosis, chronic obstructive pulmonary disease, liver and pulmonary, pancreatic fibrosis, skin fibrosis and liver fibrosis.

In a further embodiment of the invention, is provided a use of N-hydroxyamide derivatives according to Formula (I) for the preparation of a medicament for the prophylaxis and/or treatment of a disorder selected from inflammatory bowel disease, multiple sclerosis, osteoarthritis and rheumatoid arthritis.

In another further embodiment of the invention, is provided a use of N-hydroxyamide derivatives according to Formula (I) for the preparation of a medicament for the prophylaxis and/or treatment of a disorder selected from asthma, emphysema and chronic obstructive pulmonary disease.

In another further embodiment of the invention, is provided a use of N-hydroxyamide derivatives according to Formula (I) for the preparation of a medicament for the prophylaxis and/or treatment of a disorder selected from pulmonary, pancreatic, skin and liver fibrosis.

In another further embodiment of the invention, is provided a use of N-hydroxyamide derivatives according to Formula (I) for the preparation of a medicament for the prophylaxis and/or treatment of a disorder wherein the disorder is a cancer or malignancy.

In another embodiment of the invention, is provided a use of N-hydroxyamide derivatives according to Formula (I) for the modulation, in particular for the inhibition, of the matrix metalloproteinase activity. Particularly, is provided a use according to the invention wherein said matrix metalloproteinase is MMP-12.

In another embodiment, compounds according to the invention are selective inhibitors of metalloproteineases selected from MMP-2, MMP-9 and/or MMP-12 over MMP-1.

In another embodiment, the invention provides a method of treatment and/or prophylaxis of a disease comprising the administration of a compound according to Formula (I), in a patient in need thereof and wherein the disease is selected from autoimmune disorders, inflammatory diseases, cardiovascular diseases, neurodegenerative diseases, stroke, allergic and dermatologic diseases, metabolic disorders, cancer and malignancy, respiratory diseases and fibrosis, including multiple sclerosis, arthritis, rheumatoid arthritis, osteoarthritis, asthma, emphysema, pre-term labor, endometriosis, chronic obstructive pulmonary disease (COPD), liver, psoriasis, skin and pulmonary fibrosis.

In another embodiment, the invention provides a process for the preparation of a N-hydroxyamide derivative according to Formula (I), comprising the step of reacting a compound of Formula (II) with a formylating agent of formula (FA):

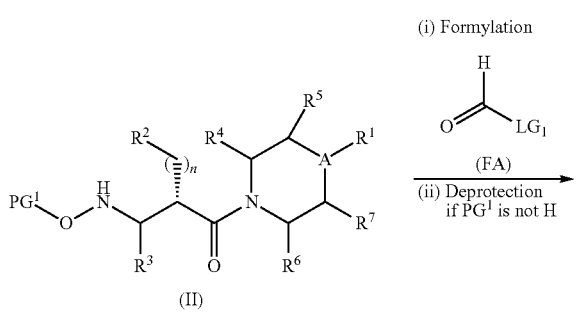

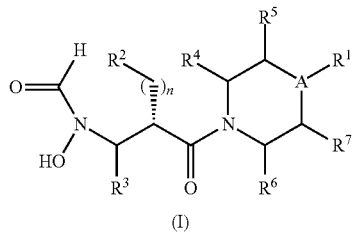

(I)

wherein $R^1$, $R^2$, $R^3$, $R^4$, $R^5$, $R^6$, $R^7$ and n are defined as above, $PG^1$ is H or a protecting group such as benzyl, t-butyl, THP, TMS, TBS and $LG_1$ is a leaving group such as —OH, —OAc, —OPiv, —OCH$_2$CN, —OCH$_2$CF$_3$, —OPh and —OPfp.

In a further embodiment, the invention provides a compound according to Formula (II) selected from the following group:

(2S)—N-(benzyloxy)-2-{[4-(4-methoxyphenyl)piperazin-1-yl]carbonyl}-4-methylpentan-1-amine;

(2S)—N-(benzyloxy)-2-[(4-biphenyl-4-ylpiperazin-1-yl)carbonyl]-4-methylpentan-1-amine.

The compounds of invention have been named according the standards used in the program program "ACD/Name" from Advanced Chemistry Development Inc., ACD/Labs (7.00 Release).

The compounds of Formula (I) are useful for the treatment and/or prophylaxis of autoimmune disorders, inflammatory diseases, cardiovascular diseases, neurodegenerative diseases, stroke, cancer and malignancy, allergic and dermatologic diseases, metabolic disorders, respiratory diseases, preterm labor, endometriosis and fibrosis, including multiple sclerosis, arthritis, rheumatoid arthritis, osteoarthritis, emphysema, chronic obstructive pulmonary disease, psoriasis, liver and pulmonary fibrosis.

In another embodiment, the compounds of the invention can be used in the treatment of autoimmune diseases, especially demyelinating diseases such as multiple sclerosis, alone or in combination with a co-agent useful in the treatment of autoimmune diseases, wherein the co-agent is for example selected from the following compounds:

(a) Interferons, e.g. pegylated or non-pegylated interferons, e.g. administered by sub-cutaneous, intramuscular or oral routes, preferably interferon beta;

(b) Glatiramer, e.g. in the acetate form;

(c) Immunosuppressants with optionally antiproliferative/antineoplastic activity, e.g. mitoxantrone, methotrexate, azathioprine, cyclophosphamide, or steroids, e.g. methylprednisolone, prednisone or dexamethasone, or steroid-secreting agents, e.g. ACTH;

(d) Adenosine deaminase inhibitors, e.g. Cladribine;

(e) Inhibitors of VCAM-1 expression or antagonists of its ligand, e.g. antagonists of the α4/β1 integrin VLA-4 and/or alpha-4-beta-7 integrins, e.g. natalizumab (ANTEGREN).

Further co-agents such as anti-inflammatory agents (in particular for demyelinating diseases such as multiple sclerosis) are described below:

A further anti-inflammatory agent is Teriflunomide which is described in WO 02/080897

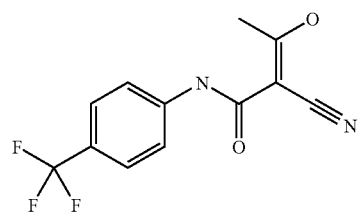

Still a further anti-inflammatory agent is Fingolimod which is described in EP-627406 and WO 2004/028521.

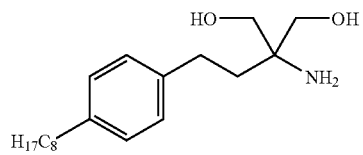

Still a further anti-inflammatory agent is Laquinimod which is described in WO 99/55678.

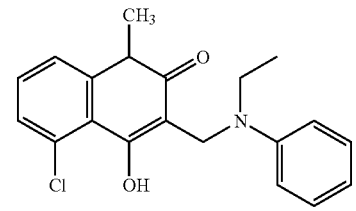

Still a further anti-inflammatory agent is Tensirolimus which is described in WO 02/28866.

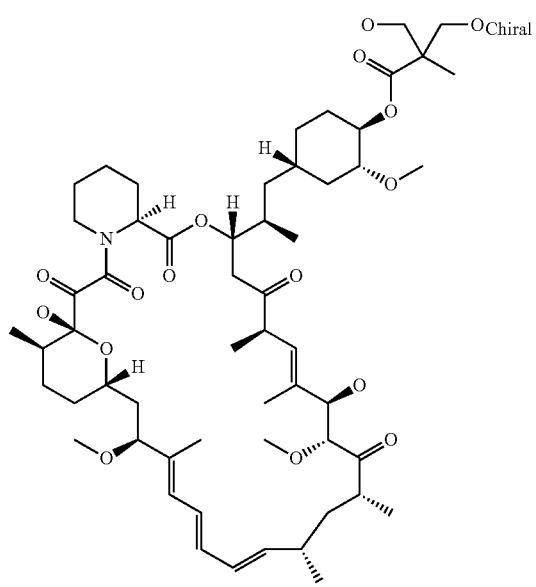

Still a further anti-inflammatory agent is Xaliprodene which is described in WO 98/48802.

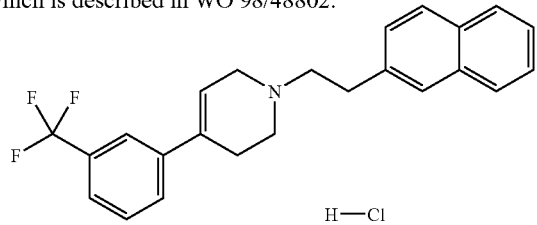

Still a further anti-inflammatory agent is Deskar Pirfenidone which is described in WO 03/068230.

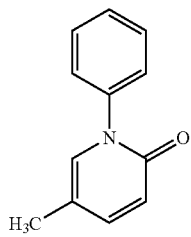

Still a further anti-inflammatory agent is the below benzothiazole derivative which is described in WO 01/47920.

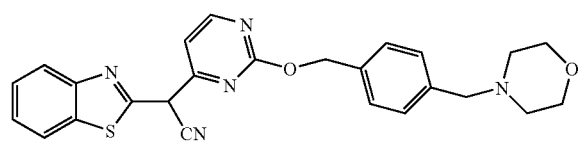

Still a further anti-inflammatory agent is the below hydroxamic acid derivative which is described in WO 03/070711.

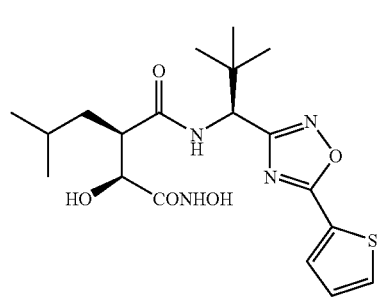

Still a further anti-inflammatory agent is MLN3897 which is described in WO 2004/043965.

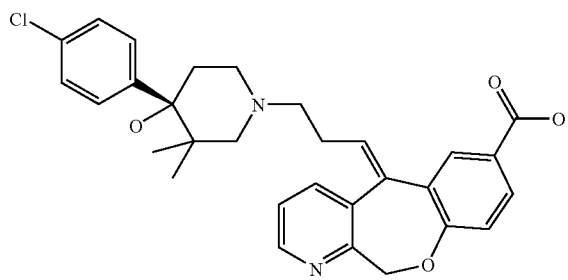

Still a further anti-inflammatory agent is CDP323 which is described in WO 99/67230.

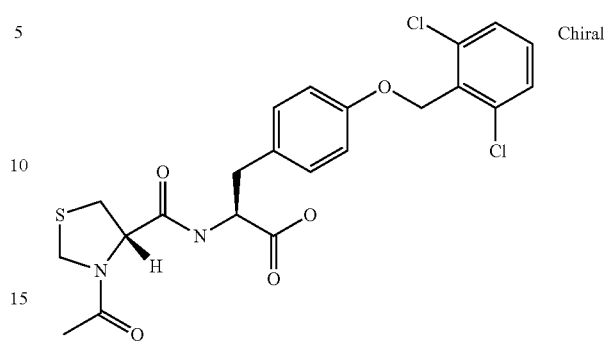

Still a further anti-inflammatory agent is Simvastatin which is described in WO 01/45698.

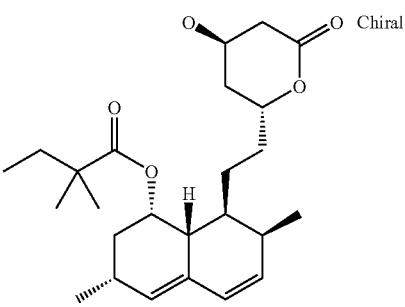

Still a further anti-inflammatory agent is Fampridine which is described in U.S. Pat. No. 5,540,938.

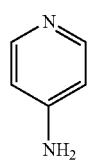

Compounds according to the present invention also comprise its tautomers, its geometrical isomers, its optically active forms as enantiomers, diastereomers and its racemate forms, as well as pharmaceutically acceptable salts thereof.

The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

When employed as pharmaceuticals, the compounds of the present invention are typically administered in the form of a pharmaceutical composition. Hence, pharmaceutical compositions comprising a compound of the invention and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, pre-measured ampoules or syringes of the liquid compositions or pills, tablets, capsules or the like in the case of solid compositions. In such compositions, the derivative of the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate-buffered saline or other injectable carriers known in the art. As above mentioned, the N-hydroxyamide derivatives of Formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

Synthesis of Compounds of the Invention:

The novel derivatives according to Formula (I) can be prepared from readily available starting materials by several synthetic approaches, using both solution-phase and solid-phase chemistry protocols. Examples of synthetic pathways for the will be described.

The following abbreviations refer respectively to the definitions below:

aq (aqueous), atm (atmosphere), Boc (tert-butoxycarbonyl), Bn (Benzyl), h (hour), g (gram), L (liter), mg (milligram), MHz (Megahertz), min. (minute), mm (millimeter), mmol (millimole), mM (millimolar), m.p. (melting point), eq (equivalent), mL (milliliter), µL (microliter), Ac (acetyl), ACN (acetonitrile), Bu (butyl), c-hex (cyclohexane), DCC (dicyclohexyl carbodiimide), DCM (dichloromethane), DIC (Diisopropyl carbodiimide), DIEA (diisopropylethylamine), DMF (dimethylformamide), DMSO (dimethylsulfoxide), ESI (electro-spray ionization), HATU (Dimethylamino-([1,2,3]triazolo[4,5-b]pyridin-3-yloxy)-methylene]-dimethyl-ammonium hexafluoro phosphate), HPLC (high performance liquid chromatography), iPr (isopropyl), LC (liquid chromatography), Me (methyl), MS (mass spectrometry), NMM (N-methyl morpholine), NMR (nuclear magnetic resonance), Pfp (petafluorophenyl), PyBOP® (Benzotriazole-1-yl-oxy-tris-pyrrolidino-phosphonium hexafluoro phosphate), rt (room temperature), Rt (retention time), TBS (tert-butyl-dimethylsilyl), TBTU (2-(1-H-benzotriazole-1-yl)-1,1,3,3-tetramethyl uromium tetrafluoro borate), TEA (triethylamine), THF (tetrahydrofuran), THP (tetrahydropyranyl), TMS (trimethylsilyl), TLC (thin layer chromatography), UV (Ultra-violet), Z (benzyloxycarbonyl).

Synthetic Approaches:

Generally, compounds of Formula (I) may be obtained by formylation of a compound of Formula (II) wherein $R^1$, $R^2$, $R^3$, $R^4$, $R^5$, $R^6$, $R^7$ and n are defined as above and $PG^1$ is H or a protecting group such as benzyl, t-butyl, THP, TMS or TBS with a formylating agent of formula (FA) (Scheme 1 below). If $PG^1$ is not H, a known deprotection step should follow or precede the formylation step.

General protocols for such a formylation are given below in the examples. The use of formylating agents (FA) are well known from those skilled in the art, wherein $LG_1$ is a leaving group such as —OH, —OAc, —OPiv, —OCH$_2$CN, —OCH$_2$CF$_3$, —OPh and —OPfp. For example, a formylating agent may be obtained by reaction between formic acid and acetic anhydride.

Scheme 1

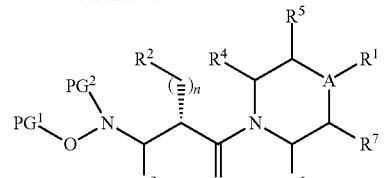

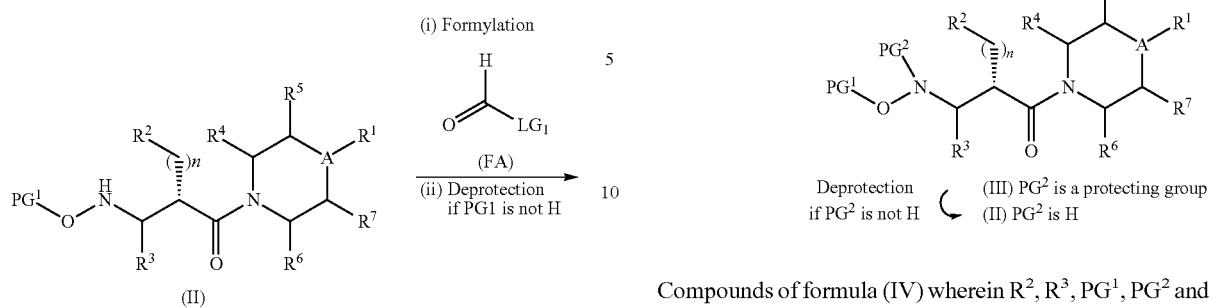

Compounds of formula (IV) wherein $R^2$, $R^3$, $PG^1$, $PG^2$ and n are as defined above can be prepared by hydrolysis of compound of formula (VI) where G is a chiral auxiliary such as the Evan's chiral oxazolidinones. Preferred conditions involve the use of lithium hydroxide in the presence of water peroxide in solvent such as THF (Scheme 3 below).

Scheme 3

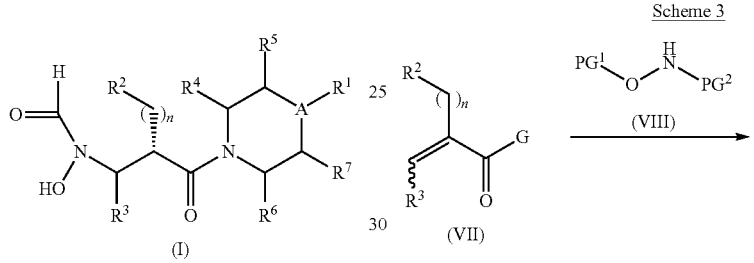

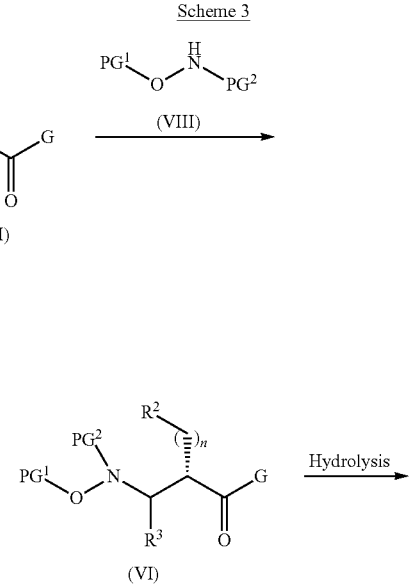

A preferred synthetic approach for the preparation of a compound of Formula (II) consists in the coupling of a carboxylic acid of formula (IV) with an amine of formula (V) wherein $R^2$, $R^3$, $PG^1$ and n are defined as above and $PG^2$ is H or a protecting group such as Boc, Z, Bn (Scheme 2 below) several protocols for such coupling are given below in the Examples, using conditions and methods well known to those skilled in the art to prepare an amide bond from an amine and a carboxylic acid or carboxylic acid derivative (e.g. acid chloride), with or without standard coupling agents, such as e.g. DIC, EDC, TBTU, DCC, HATU, PyBOP®, Isobutyl chloroformate, 1-methyl-2-chloropyridinium iodide (Mukaiyama's reagent) or others in the presence or not of bases such as TEA, DIEA, NMM in a suitable solvent such as DCM, THF or DMF. When $PG^2$ is not H, a known deprotection step should follow or precede the coupling step (Scheme 2 below).

Compounds of formula (VI) can be prepared by the diastereoselective addition of hydroxylamine or a hydroxylamine derivative (VIII) wherein $PG^1$ is H or a protecting group such as benzyl, t-butyl, THP, TMS, TBS and $PG^2$ is H or a protecting group such as Boc, Z, Bn.

Compound of formula (VII) can be obtained by coupling the carboxylic acid of formula (IX) wherein $R^2$, $R^3$ and n are defined as above with the chiral auxiliary (GH) following conditions well known by a person skilled in the art (Scheme 4 below). Compound of formula (IX) can be obtained following protocols described in the literature (e.g. WO 02/102790).

Scheme 2

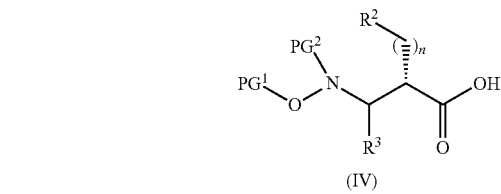

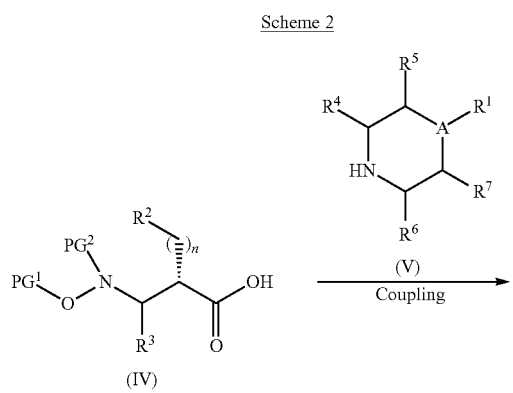

Scheme 4

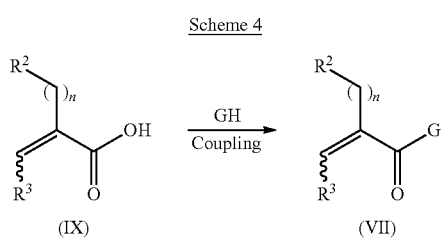

Compounds of Formula (I) and its precursors of Formulae (II), (III), (IV), (V) and (VI) contain at least one chiral center (3S), and all individual optically active forms and combinations of these are disclosed in the invention, as well as their corresponding racemates.

The processes outlined in the above Schemes, in particular Schemes 1, 2 and 3, afford compounds of Formula (I) and its precursors of Formulae (II), (III), (IV) and (VI) as pure stereoisomer, or as in racemic form or as mixtures of diastereoisomers. In the latter case, pure stereoisomers can be obtained from stereoisomer mixtures using procedures well known to those skilled in the art, including for example separation of enantiomers by chiral HPLC, or crystallization and/or chromatography for mixture of diastereoisomers.

For example, an alternative preparation for compound of formula (IV) wherein $R^2$, $R^3$, $PG^1$, $PG^2$ and n are defined as above can be the enantiomeric or diastereomeric separation of a mixture of compounds of formula (IVa), obtained by Michael addition of hydroxylamine (VIII) derivatives of formula (VIII) on the unsaturated ester of formula (VIIa) wherein $R^2$, $R^3$, $PG^1$, $PG^2$ and n are defined as above and $R^8$ is H or an $C_1$-$C_6$ alkyl group such as methyl or ethyl (Scheme 5 below).

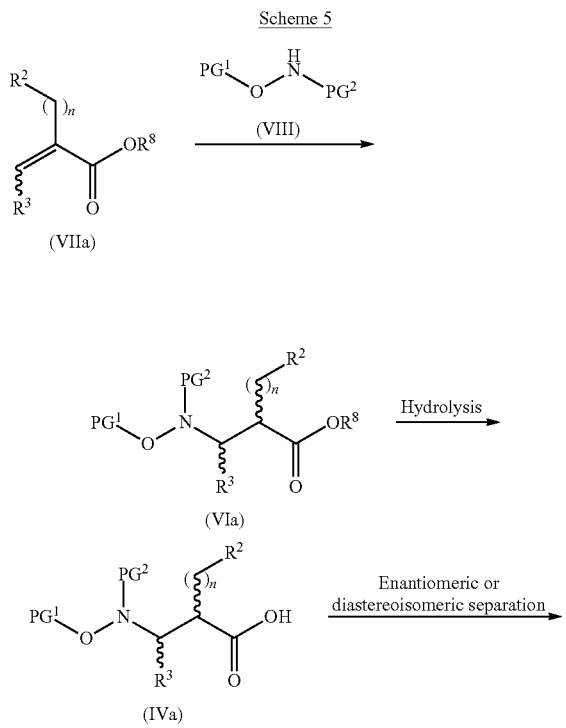

According to a further general process, compounds of Formula (I) can be converted to alternative compounds of Formula (I), employing suitable interconversion techniques well known by a person skilled in the art.

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, $3^{rd}$ Edition 1999. Those skilled in the art will recognize that certain reactions are best carried out when potentially reactive functionality on the molecule is masked or protected, thus avoiding side reactions and/or increasing the yield of the reaction. Examples of protecting group moieties may be found in *Philip J Kocienski*, 1994 above and in Greene et al., 1999, above. The need and choice of protecting groups for a particular reaction is known to those skilled in the art and depends on the nature of the functional group to be protected (hydroxy, amino, carboxy, etc.), the structure and the stability of the molecule of which the substituent is part of the reaction conditions.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

The following reagents commercially available were used:

Isobutyl malonic acid (prepared as described in Kortylewicz et al., 1990, *J. Med. Chem.* 33, 263-273), di-tert-butyl dicarbonate (from Aldrich), 1-biphenyl-4-ylpiperazine (From Apollo), 1-(4-methoxyphenyl)-piperazine (From Chess), HATU (from Aldrich).

Intermediate A (2S)-2-{[(benzyloxy)(tert-butoxycarbonyl)amino]methyl}-4-methyl pentanoic acid

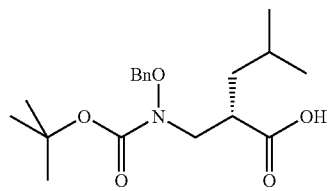

Step a) Formation of tert-butyl((2S)-2-{[(4R)-4-benzyl-2-oxo-1,3-oxazolidin-3-yl]carbonyl}-4-methylpentyl)(benzyloxy)carbamate

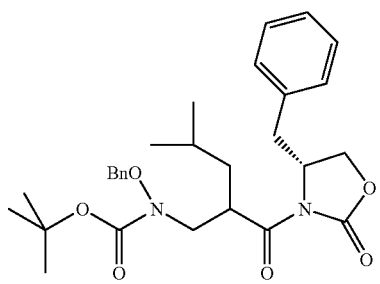

To a solution of 4-benzyl-3-[2-(benzyloxyamino-methyl)-4-methyl-pentanoyl]-oxazolidin-2-one (1.0 g; 2.44 mmol; 1.0 eq. prepared following the protocols described in WO 02/102790 but starting from isobutyl malonic acid) and di-tert-butyl dicarbonate (585 mg; 2.7 mmol; 1.1 eq.) in DCM (10 mL) was added triethylamine (416 μL; 2.9 mmol; 1.2 eq.) and the reaction mixture stirred overnight at room temperature. DMAP (0.1 eq.) and then di-tert-butyl dicarbonate (200 mg) were added and the mixture stirred at room temperature overnight. An aqueous solution of HCl (1 N) was added and the reaction mixture extracted with EtOAc (3×). The combined organic layers were dried over MgSO₄, filtered and evaporated to give a colorless oil. Purification by column chromatography (Silicagel, 13% EtOAc in c-Hex) gave the title product as a colorless oil (920 mg, 74%). HPLC, Rt: 5.33 min (purity: 88.9%).

Step b) Formation of (2S)-2-{[(benzyloxy)(tert-butoxycarbonyl)amino]methyl}-4-methyl pentanoic acid A solution of tert-butyl((2S)-2-{[(4R)-4-benzyl-2-oxo-1,3-oxazolidin-3-yl]carbonyl}-4-methylpentyl)(benzyloxy)carbamate (1.66 g, 3.25 mmol), LiOH (156 mg, 6.5 mmol, 2 eq.) and an aqueous solution of H₂O₂ (30%, 1.33 mL, 4 eq.), was stirred overnight. A saturated solution of Na₂SO₃ was added at 0° C. The mixture was extracted with a saturated solution of NaHCO₃, washed with DCM (3×). The aqueous layer was saturated with NaCl, acidified up to pH 2 with an aqueous solution of HCl (5 N), then extracted with DCM (2×), EtOAc (2×), Et₂O (2×). The combined organic layers were dried over MgSO₄, filtered and evaporated to give 300 mg of the title product as a colorless oil used as such in the next step. M⁻(LC-MS (ESI)): 350.3.

EXAMPLE 1

Hydroxy((2S)-2-{[4-(4-methoxyphenyl)piperazin-1-yl]carbonyl}-4-methyl pentyl)formamide (1)

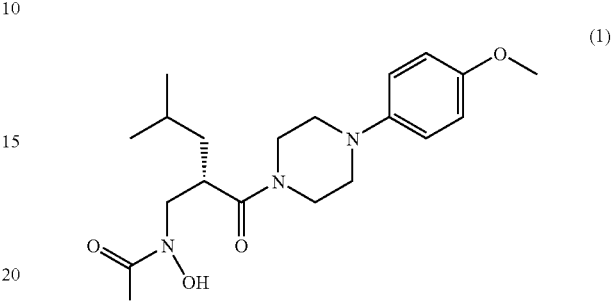

(1)

Step a) Formation of tert-butyl(benzyloxy)((2S)-2-{[4-(4-methoxyphenyl)piperazin-1-yl]carbonyl}-4-methylpentyl)carbamate

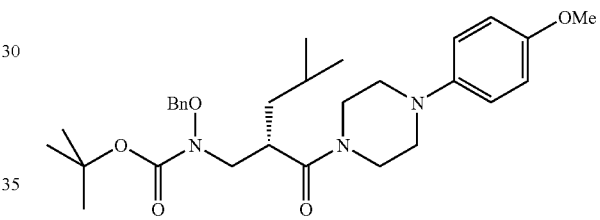

To a cold (0° C.) solution of (2S)-2-{[(benzyloxy)(tert-butoxycarbonyl)amino]methyl}-4-methylpentanoic acid (Intermediate A, 120 mg; 0.34 mmol; 1.0 eq.) and DIEA (115 mg, 0.9 mmol, 2.1 eq.) in DMF (3 mL) was added at once HATU (124 mg, 0.47 mmol, 1.1 eq.). The resulting solution was stirred 2 min at 0° C., then 1-(4-methoxyphenyl)-piperazine (72 mg; 0.38 mmol; 1.1 eq.) was added. The resulting mixture was stirred overnight at room temperature. Et₂O was added and the mixture was washed with water (3×), dried over MgSO₄, filtered and evaporated to give the title compound as an oil. Purification by column chromatography (Silicagel, gradient from 25% EtOAc up to 33% EtOAc in c-Hex) gave the title product as a colorless oil (110 mg, 61%). HPLC, Rt: 4.04 min (purity: 100%). M⁺(LC-MS (ESI)): 526.3.

Step b) Formation of (2S)—N-(benzyloxy)-2-{[4-(4-methoxyphenyl)piperazin-1-yl]carbonyl}-4-methylpentan-1-amine

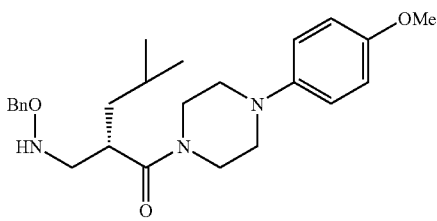

A solution of tert-butyl(benzyloxy)((2S)-2-{[4-(4-methoxyphenyl)piperazin-1-yl]carbonyl}-4-methylpentyl)carbamate (134 mg; 0.25 mmol; 1.0 eq.) and HCl 4M in dioxan (0.938 mL, 15 eq.) in DCM (1 mL) was stirred overnight at room temperature. The solvents were evaporated to give the title product as a yellow oil (130 mg, 100%). HPLC, Rt: 2.9 min (purity: 95.9%). M$^+$(LC-MS (ESI)): 426.4.

Step c) Formation of N-(benzyloxy)-N-((2S)-2-{[4-(4-methoxyphenyl)piperazin-1-yl]carbonyl}-4-methylpentyl)formamide

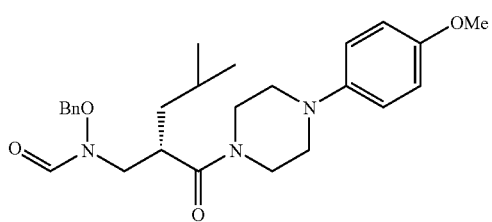

To a solution of (2S)—N-(benzyloxy)-2-{[4-(4-methoxyphenyl)piperazin-1-yl]carbonyl}-4-methylpentan-1-amine (122 mg; 0.29 mmol; 1.0 eq.) and triethylamine (123 µL; 0.86 mmol; 3.0 eq.) in THF (2 mL) was added formic acetic anhydride (63 mg, 0.72 mmol, 2.5 eq., prepared as described in Krimen et al., in *Organic Syntheses Coll. Vol* 6, p8. The solution was stirred for 4.5 h at room temperature. The solvents were evaporated and the residue purified by column chromatography (Silicagel, 1/1 EtOAc/c-Hex) to give the title product as a colorless oil (105 mg, 81%). HPLC, Rt: 3.17 min (purity: 100%). M$^+$(LC-MS (ESI)): 454.4.

Step d) Formation of N-hydroxy-N-((2S)-2-{[4-(4-methoxyphenyl)piperazin-1-yl]carbonyl}-4-methylpentyl)formamide A solution of N-(benzyloxy)-N-((2S)-2-{[4-(4-methoxyphenyl)piperazin-1-yl]carbonyl}-4-methylpentyl)formamide (100 mg, 0.22 mmol) was hydrogenated under 1 atm of hydrogen in the presence of Pd/C (10%, 23 mg, 0.02 mmol, 0.1 eq.) for 2 h at room temperature. The mixture was filtered on a bed of cellite, evaporated to give the title product as an orange foam (60 mg, 75%). HPLC, Rt: 1.95 min (purity: 100%). M$^+$(LC-MS (ESI)): 364.4.

EXAMPLE 2

{(2S)-2-[(4-biphenyl-4-ylpiperazin-1-yl)carbonyl]-4-methylpentyl}hydroxyformamide (2)

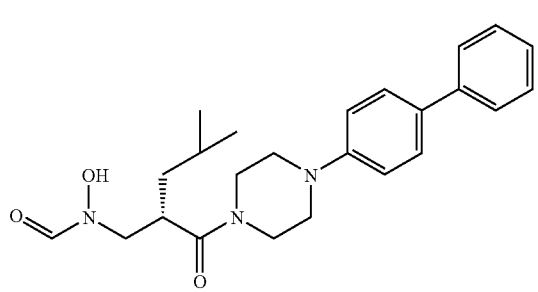

(2)

Step a) Formation of tert-butyl(benzyloxy){(2S)-2-[(4-biphenyl-4-ylpiperazin-1-yl)carbonyl]-4-methylpentyl}carbamate

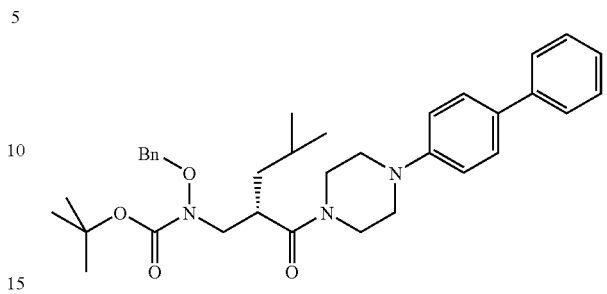

The title product was obtained following the protocol of Example 1 (step a), but starting from Intermediate 1 (300 mg, 0.85 mmol) and 1-biphenyl-4-ylpiperazine (357 mg, 0.94 mmol, 1.1 eq.). Purification by column chromatography (Silicagel, gradient from 33% EtOAc up to 50% EtOAc in c-Hex) gave the title product as a colorless oil (240 mg, 49%). HPLC, Rt: 5.33 min (purity: 100%). M$^+$(LC-MS (ESI)): 572.1.

Step b) Formation of (2S)—N-(benzyloxy)-2-[(4-biphenyl-4-ylpiperazin-1-yl)carbonyl]-4-methylpentan-1-amine

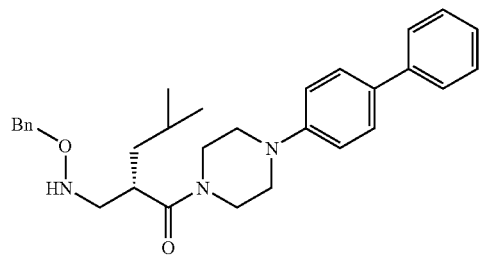

The title product was obtained following the protocol of Example 1 (step b), but starting from tert-butyl(benzyloxy){(2S)-2-[(4-biphenyl-4-ylpiperazin-1-yl)carbonyl]-4-methylpentyl}carbamate (232 mg; 0.41 mmol; 1.0 eq.) as a brown solid (219 mg, 99%). HPLC, Rt: 4.19 min (purity: 93.6%). M$^+$(LC-MS (ESI)): 472.4.

Step c) Formation of N-(benzyloxy)-N-{(2S)-2-[(4-biphenyl-4-ylpiperazin-1-yl)carbonyl]-4-methylpentyl}formamide

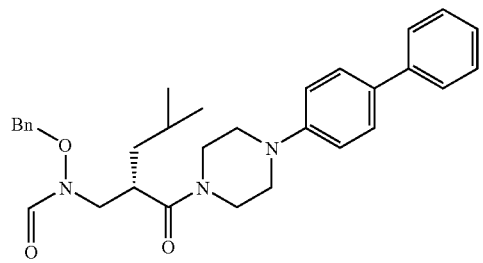

The title product was obtained following the protocol of Example 1 (step c), but starting from tert-butyl(benzyloxy){(2S)-2-[(4-biphenyl-4-ylpiperazin-1-yl)carbonyl]-4-methylpentyl}carbamate (219 mg, 0.46 mmol) and a preformed mixture of formic acid (875 µL; 23.2 mmol; 50 eq.) and acetic anhydride (220 µl; 2.32 mmol; 5.0 eq.) (mixture formed at 0° C. for 30 min). Purification by column chromatography (Silicagel, gradient from 33% EtOAc up to 50% EtOAc in c-Hex) gave the title product as a white solid (120 mg, 52%). HPLC, Rt: 4.60 min (purity: 99.7%). M⁺(LC-MS (ESI)): 500.4.

Step d) Formation of N-{(2S)-2-[(4-biphenyl-4-ylpiperazin-1-yl)carbonyl]-4-methylpentyl}-N-hydroxyformamide The title product was obtained following the protocol of Example 1 (step d), but starting from N-(benzyloxy)-N-{(2S)-2-[(4-biphenyl-4-ylpiperazin-1-yl)carbonyl]-4-methylpentyl}formamide (110 mg; 0.22 mmol; 1.0 eq.) as a white powder (62 mg, 78%). HPLC, Rt: 3.57 min (purity: 88.2%). M⁺(LC-MS (ESI)): 410.0, M⁻(LC-MS (ESI)): 408.3.

Biological Assays:

The compounds of the present invention may be subjected to the following assays:

EXAMPLE 3

Enzyme Inhibition Assays

Compounds of the invention were tested to assess their activities as inhibitors of MMP-1, MMP-2, MMP-9, MMP-14 and MMP-12.

MMP 9 Assay Protocol

Compounds of the invention were tested for inhibitory activity against 92 kDa gelatinase (MMP-9) in an assay using a coumarin-labeled peptide substrate, (7-methoxycoumarin-4-yl)acetyl-Pro-Leu-Gly-Leu-(3-[2,4-dinitrophenyl]-L-2,3 diaminopropionyl)-Ala-Arg-NH2 (McaPLGLDpaAR) (Knight et al, *FEBS Lett.* 1992; 263-266).

Stock solutions were made up as follows: Assay Butter: 100 mM Tris-HCl pH 7.6 containing 100 mM NaCl, 10 mM $CaCl_2$, and 0.05% Brij 35.

Substrate: 0.4 mM McaPLGLDpaAR (from Bachem) (0.437 mg/ml) stock solution in 100% DMSO (stored at −20° C.). Dilute to 8 µM in assay butter.

Enzyme: Recombinant human 92 kDa gelatinase (MMP-9; APMA (4-aminophenyl mercuric acetate)-activated if necessary) appropriately diluted in assay butter.

Test Compounds were prepared initially as 10 mM compound solution in 100% DMSO, diluted to 1 mM in 100% DMSO, then serially diluted 3-fold in 100% DMSO across columns 1-10 of a 96-well microtitre plate Assay concentration range, 100 µM (column 1) to 5.1 nM (column 10).

The assay was performed in a total volume of 100 µL per well in 96-well microtitre plates. Activated enzyme (20 µL) was added to the wells followed by 20 µL of assay butter. Appropriate concentrations of test compounds dissolved in 10 µL of DMSO were then added followed by 50 µL of McaPLGLDpaAR (8 µM, prepared by dilution of DMSO stock in assay butter). For each as say ten concentrations of test compound were examined in duplicate. Control wells lack either enzyme or test compound. The reactions were incubated at 37° C. for 2 hours. The fluorescence at 405 nm was measured immediately with an SLT Fluostar fluorometer (SL T Labinstruments GmbH, Grödig, Austria) using 320 nm excitation, without stopping the reaction.

The effect of the test compound was determined from the dose response curve generated by the 10 duplicate concentrations of inhibitor. The $IC_{50}$ (the concentration of compound required to give a 50% decrease in enzyme activity) was obtained by fitting data to the equation, $Y=a+((b-a)/(1+(c/X)^d))$. (Y=inhibition achieved for a particular dose; X=the dose in nM; a=minimum y or zero % inhibition; b=maximum y or 100% inhibition; c=is the $IC_{50}$; d=is the slope). The result was rounded to one significant figure.

MMP-12 Assay Protocol

Compounds of the invention were tested for inhibitory activity against metalloelastase (MMP-12) in an assay using a coumarin-labelled peptide substrate, (7-methoxycoumarin-4-yl)acetyl-Pro-Leu-Gly-Leu-(3-[2,4-dinitrophenyl]-L-2,3-diaminopropionyl)-Ala-Arg-NH₂ (McaPLGLDpaAR) (Knight et al, 1992, above). The protocol for this assay was as described for the MMP-9 assay above.

MMP-1 Assay protocol

Compounds of the invention were tested for inhibitory activity against collagenase (MMP-1) in an assay using a coumarin-labelled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (Mca PLGLDpaAR) (Knight et al, 1992, above). The protocol for this assay was as described for the MMP-9 assay above.

MMP-14 Assay Protocol

Compounds of the invention were tested for inhibitory activity against MMP-14 in an assay using a coumarin-labelled peptide substrate, (7-methoxycoumarin-4-yl)acetyl-Pro-Leu-Gly-Leu-(3-[2,4-dinitrophenyl]-L-2,3diaminopropionyl)-Ala-Arg-NH₂ (Mca PLGLD paAR) (Knight et al, 1992, above). The protocol for this assay was as described for the MMP-9 assay above.

MMP-2 Assay Protocol

Compounds of the invention were tested for inhibitory activity against gelatinase A (MMP-2) in an assay using a coumarin-labelled peptide substrate, (7-methoxycoumarin-4-yl)acetyl-Pro-Leu-Gly-Leu-(3-[2,4-dinitrophenyl]-L-2,3diaminopropionyl)-Ala-Arg-NH2 (Mca PLGLDpaAR) (Knight et al, 1992, above). The protocol for this assay was as described for the MMP-9 assay above.

The results are expressed in terms of $IC_{50}$ (the concentration of compound required to give a 50% decrease in enzyme activity) and are presented in Table 1 below.

TABLE 1

| | $IC_{50}$ on different MMPs: | | |
|---|---|---|---|
| Example | MMP-1 $IC_{50}$ (nM) | MMP-2 $IC_{50}$ (nM) | MMP-12 $IC_{50}$ (nM) |
| Example 1 | >5000 | 13 | 68 |
| Example 2 | >5000 | 9 | 8 |

EXAMPLE 4

IL-2-Induced Peritoneal Recruitment of Lymphocytes

Administration of IL-2 intraperitoneally causes migration of lymphocytes into the intraperitoneal cavity. This is a model for the cellular migration that occurs during inflammation.

Protocol

C3H/HEN mice (Elevage Janvier, France) were intraperitoneally injected with IL-2 (20 µg/kg, in saline).

Compounds of the invention were suspended in 0.5% carboxymethylcellulose (CMC)/0.25% tween-20 and were administered by s.c. or p.o. route (10 ml/kg) 15 min prior to administration of IL-2.

Twenty-four hours after administration of IL-2, peritoneal white blood cells were collected by 3 successive lavages of the peritoneal cavity with 5 ml phosphate buffered saline (PBS)-1 mM EDTA (+4° C.). The suspension was centrifuged (1700 g×10 min at +4° C.). The resulting pellet was suspended in 1 ml PBS-1 mM EDTA. Lymphocytes were identified and counted using a Beckman/Coulter counter.

Experimental Design

The animals were divided into 6 groups (6 mice each group):

Group 1: (baseline) received 0.5% CMC/0.25% tween-20 (vehicle of compound of the invention) and saline (vehicle of IL-2);
Group 2: (control IL-2) received 0.5% CMC/0.25% tween-20 and injection of IL-2;
Group 3: Experimental group (Compound of the invention Dose 1) received a compound of the invention and injection of IL-2;
Group 4: Experimental group (Compound of the invention Dose 2) received a compound of the invention and injection of IL-2;
Group 5: Experimental group (Compound of the invention Dose 3) received a compound of the invention and injection of IL-2;
Group 6: Reference group received reference compound dexamethasone and injection of IL-2.

Calculation

Inhibition of lymphocyte recruitment was calculated as follows:

$$\% \text{ inhibition} = \frac{1 - (LyX - Ly1)}{(Ly2 - Ly1)} \times 100\%$$

Where Ly 1=Number of lymphocytes in group 1 (E3 µl), Ly 2=Number of lymphocytes in group 2 (E3/µl), Ly X=Number of lymphocytes in group X (3-5)(E3/µl).

The results for compounds according to Formula (I) are presented in Table 2 below.

TABLE 2

Percentage of inhibition of IL-2-induced peritoneal recruitment of lymphocytes by compounds of the invention:

| Example | Dose (mg/kg) | Route | % inhibition |
|---------|--------------|-------|--------------|
| Example 1 | 3 | p.o. | 35 ± 10 |

EXAMPLE 5

CCl$_4$-Induced Liver Fibrosis Model

Carbon tetrachloride (CCl$_4$) induces liver fibrosis when administered intraperitoneally (Bulbena O, Culat J, Bravo M L., *Inflammation* 1997 October; 21(5):475-88). Compounds of the invention can be evaluated for their ability to prevent the CCl$_4$-induced formation of fibrotic tissue.

Animals

Male Sprague-Dawley rats, 7 weeks old, weight approx. 300 g from Charles River/Iffa-Crédo, St-Germain/l'Arbresle, France.

Rats are acclimatised for 5 days before commencing experiments, in air-conditioned rooms, 2 animals per cage, Temperature: 22° C.±2, Relative humidity: 55%±10 Light: 12 hour cycle (7 a.m. -7 p.m.), Cage: MAKROLON cage 42.5x26.6x15 on each fitted with a stainless steel cover-feed rack.

The study involves the following groups of 8 animals each, as indicated below.

Group 1: "Sham" animals receive CCl$_4$ vehicle (i.p.) and once daily, the vehicle of test substance (s.c.)
Group 2: Positive control group receives CCl$_4$ (i.p.), and once daily, the vehicle of the test substance (s.c.)
Group 3: Experimental group receives CCl$_4$ (i.p.), and once daily, 2 mg/kg s.c. of compound according to the invention.
Group 4: Experimental group receives CCl$_4$ (i.p.), and once daily, 10 mg/kg s.c. of the compound according to the invention.
Group 5: Experimental group receives CCl$_4$ (i.p.) and once daily, 20 mg/kg s.c. of the compound according to the invention.

Rats were labeled on their tails. The labels are checked and renewed, if necessary, after every CCl$_4$ injection.

Procedure

CCl$_4$ (Prolabo) in olive oil is administered every 3 days for three weeks by intra-peritoneal injection (0.25 ml CCl$_4$ kg body weight, diluted in oil 1:1 vol:vol for a total volume of 0.5 ml/kg). Animals are weighed daily. If body weight decreased by more than 10% of the initial weight, the animal is excluded from the study. Vehicles and compound are used as follows:

CCl$_4$ was administered in olive oil (Prolabo) at a 1:1 dilution;
The compound of the invention is suspended in 0.25% Tween-80 and 0.25% carboxymethylcellulose in sterile 0.9% NaCl. The solution is kept at 4° C. throughout the experiment and used each day to prepare the suspensions.

The compound of the invention is administered daily by subcutaneous (s.c.) injection at a volume of administration of 5 ml/kg. Groups 1 and 2 are dosed s.c. with 5 ml/kg of vehicle. Freshly prepared solutions are used on each day of the experiment. Administrations are carried out each day at the same time.

The treatment of groups of this study is started for each animal at the time of the first CCl$_4$ administration and is continued for 21 consecutive days. The last administration of test substances or vehicle is done 1 day before the sacrifice of the animals.

Results

Death are reported, date and supposed cause are reported.

Serum Enzyme Levels

Animals are killed 21 days following the first CCl$_4$ administration by isofurane inhalation. Blood is withdrawn individually at the time of sacrifice, i.e. one day after the last administration of test substance or vehicle. Blood is centrifuged at 4° C. Plasma is carefully collected and aliquoted in 3 fractions. Plasma aspartate amino transferase (ASAT) and alanine amino transferase (ALAT) levels are measured in order to assess liver necrosis. Increased ASAT and ALAT levels in serum are associated with liver impairment. Average ASAT and ALAT levels for control animals and those treated with the compound of the invention at three different dosages are reported.

Histological Evaluation of Liver Fibrosis

Liver fibrosis is evaluated by measuring the area of fibrosis in the liver using microchotomy. Results are reported as percentage area that is fibrotic.

The liver is removed, the three lobes are dissected and samples are removed and either fixed in 10% formaldehyde or frozen at −80° C.

Liver sections are embedded in paraffin blocks. Sectioning and staining with Sirius red are performed. Quantification of the fibrosis in liver is carried out on a minimum of 3 sections taken from different locations in the liver. The quantitative analysis is performed using an image analyser (Imstar) and the software Morphostar.

Average area percentages of fibrosis in the livers of animals in the different groups are calculated.

EXAMPLE 6

Chronic Obstructive Pulmonary Disease (COPD) model

Compounds of the invention can be evaluated for their ability to prevent cigarette smoke-induced COPD.

Female AJ mice (Harlan, 17-25 g) are exposed daily to cigarette smoke (CS) for 11 consecutive days in groups of 5, in individual clear chambers. Animals are weighed prior to treatment, on day 6 of exposure and on day 12. The CS was generated using 1R1 cigarettes purchased from the Institute of Tobacco Research, University of Kentucky, USA and is allowed to enter the chambers at a flow rate of 100 ml/min. In order to minimise any potential problems caused by repeated exposure to a high level of daily CS, the exposure of the mice to TS is increased gradually over the time to a maximum of 6 cigarettes from day 5 to day 11 (approximately 48 min exposure). A sham group of mice is also exposed to air on a daily basis for equivalent lengths of time as controls (no CS exposure).

Treatment

Compounds of the invention are prepared in 0.5% carboxymethylcellulose Na salt (CMC, Sigma reference C-4888) as vehicle. Animals are orally dosed twice daily by gavage in a dose volume of 5 ml/kg, 1 h prior to air or CS exposure and 6 h after the cessation of the exposure. Sham animals (n=10) received vehicle and are exposed to air for up to a maximum of 50 minutes per day. The control group (n=10) received vehicle and is exposed to CS (up to a maximum of 6 cigarettes per day). Additional groups are exposed to CS (from up to a maximum of 6 cigarettes per day) and treated with one of the test compounds or the reference compound.

Bronchoalveolar lavage and Cytospin analysis

Twenty-four hours after the last CS exposure, bronchoalveolar lavage is performed as follows:

The trachea is dissected under deep anesthesia (sodium pentobarbitone) and cannulated using a Portex nylon intravenous cannula shortened to approximately 8 mm. Phosphate buffered saline (PBS, Gibco) containing 10 units/ml heparin (0.4 ml) is gently instilled and withdrawn 3 times. The lavage fluid is placed in an Eppendorf tube and kept on ice prior to subsequent determinations. Then, lavage fluid is separated from cells by centrifugation. The supernatant is removed and frozen for subsequent analysis. The cell pellet is resuspended in PBS and total cell numbers are calculated by counting a stained aliquot (Turks stain) under a microscope using a haemocytometer.

Differential cell count is then performed as follows: The residual cell pellet is diluted to approximately 105 cells per ml. A volume of 500 µl is placed in the funnel of a cytospin slide and is centrifuged for 8 min at 800 rpm. The slide is air-dried and stained using 'Kwik-Diff' solutions (Shandon) following purchaser instructions. Slides are dried and coverslipped and differential cell count is done using light microscopy. Up to 400 cells are counted for each slide. Cells were differentiated using standard morphometric techniques.

Statistical Analysis

The mean +/−S.D. is calculated for each experimental group. Results are analyzed using a one-way analysis of variance (ANOVA), followed by a Bonferroni correction for multiple comparisons. Statistical significance is considered with $p<0.05$.

EXAMPLE 7

Experimental Allergic Encephalomyelitis (EAE) Model

Compounds according to the invention can be evaluated for their activity in a model for multiple sclerosis in mice.

Animals

C57BL/6NCrlBR female mice are used. Mice are kept in wire cages (cm 32×14×13 h) with stainless steel feeders and fed on a standard diet (4RF21, Charles River, Italy) and water ad libitum. From day 7, wet pellets are also placed every day on the bottom of the cage. Plastic bottles are used in addition to the automatic water system.

Experimental Procedure

Mice are immunized (day=0) by injecting s.c. in the left flank 0.2 ml of an emulsion composed of 200 µg $MOG_{35-55}$ peptide (Neosystem, Strasbourg, France) in Complete Freund's Adjuvant (CFA, Difco, Detroit, U.S.A.) containing 0.5 mg of *Mycobacterium tuberculosis*. Immediately after, they receive an i.p. injection of 500 ng pertussis toxin (List Biological Lab., Campbell, Calif., U.S.A.) dissolved in 400 µL of buffer (0.5 M NaCl, 0.017% Triton X-100, 0.015 M Tris, pH=7.5). On day 2, the animals are given a second injection of 500 ng pertussis toxin.

On day 7, the mice receive a second dose of 200 µg of $MOG_{35-55}$ peptide in CFA injected s.c. in the right flank. Starting approximately from day 8-10, this procedure results in a progressing paralysis, arising from the tail and ascending up to the forelimbs. Animals are individually weighed and are examined for the presence of paralysis that is scored according to the following score-system (1):

0=no signs of disease 0.5=partial tail paralysis

1=tail paralysis 1.5=tail paralysis+partial unilateral hindlimb paralysis

2=tail paralysis+bilateral hindlimb weakness or partial paralysis 2.5=tail paralysis+partial hindlimb paralysis (lowered pelvi)

3=tail paralysis+complete hindlimb paralysis 3.5=tail paralysis+hindlimb paralysis+incontinence 4=tail paralysis+hindlimb paralysis+weakness or partial paralysis of forelimbs 5=moribund or dead Mortality and clinical signs are monitored daily in each group of treatment, by a technician who is unaware of treatments.

Daily treatment with compounds, their vehicle or with a reference compound starts on day 7 and continued for 15 or 21 consecutive days in all groups.

Histopathological Examination

At the end of the treatment period, each animal is anesthetised with sodium pentobarbital and is transcardially perfused-fixed with 4% paraformaldehyde via the left ventricle. Fixed spinal cords are then carefully dissected out.

Spinal cord slices are embedded in paraffin blocks. Sectioning and staining with hematoxylin and eosin and CD45 staining for inflammation, and with Kluver-PAS (Luxol fast blue plus Periodic Acid Schiff staining) and Bielchowski's staining for the detection of demyelination and axonal loss, are performed.

In the spinal cord, the total area of all slices is measured for each animal as points of intersection of a 10×10 grid at a magnification of 0.4×0.4 mm per grid. The perivascular inflammatory infiltrates are counted in each slice in order to obtain a total value for each animal and evaluated as number of infiltrates per mm². Demyelination and axonal loss areas are measured for each animal as points of intersection of 10×10 grid at a magnification of 0.1×0.1 mm per grid and are expressed as a percentage of total demyelination area over the total area of the slices.

Data Evaluation and Statistical Analysis

The results of clinical and histopathological observations are expressed as the mean (±SEM) scores in each treatment group. Values obtained in the test drug-treated groups are compared with that of the positive control group. Significance of differences among groups relating to clinical score are analysed by one-way ANOVA, followed in case of significance ($p<0.05$) by Fisher test.

Differences among groups for the presence of perivascular inflammatory infiltrates and the extent of demyelination and axonal loss in the spinal cord as well as body weight data are analysed by one-way ANOVA, followed in case of significance ($p<0.05$) by Fisher test.

EXAMPLE 8

Preparation of a Pharmaceutical Formulation

The following formulation examples illustrate representative pharmaceutical compositions according to the present invention being not restricted thereto.

Formulation 1—Tablets

A compound of the invention is admixed as a dry powder with a dry gelatin binder in an approximate 1:2 weight ration. A minor amount of magnesium stearate is added as a lubricant. The mixture is formed into 240-270 mg tablets (80-90 mg) of active N-hydroxyamide derivative per tablet) in a tablet press.

Formulation 2—Capsules

A compound of the invention is admixed as a dry powder with a starch diluent in an approximate 1:1 weight ratio. The mixture is filled into 250 mg capsules (125 mg of active N-hydroxyamide derivative per capsule).

Formulation 3—Liquid

A compound of the invention (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active N-hydroxyamide derivative) in a tablet press.

Formulation 5—Injection

A compound of the invention is dissolved in a buffered sterile saline injectable aqueous medium to a concentration of approximately 5 mg/ml.

The invention claimed is:

1. A compound according to Formula (II):

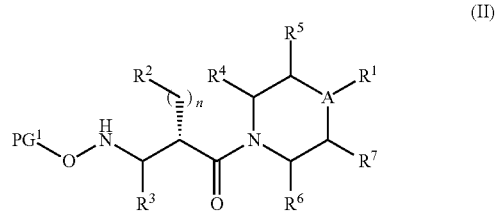

(II)

wherein:

A is N;

$R^1$ is selected from H, $C_1$-$C_6$ alkyl, $C_2$-$C_6$ alkenyl, $C_2$-$C_6$ alkynyl, $C_3$-$C_8$-cycloalkyl, heterocycloalkyl, aryl, heteroaryl, $C_3$-$C_8$-cycloalkyl $C_1$-$C_6$ alkyl, heterocycloalkyl $C_1$-$C_6$ alkyl, heteroaryl $C_1$-$C_6$ alkyl, amino or alkoxy;

$R^2$ is selected from H, $C_1$-$C_6$ alkyl, $C_2$-$C_6$ alkenyl, $C_2$-$C_6$ alkynyl, $C_3$-$C_8$-cycloalkyl, heterocycloalkyl, alkoxy, aryl or heteroaryl;

$R^3$ is selected from H, $C_1$-$C_6$ alkyl, $C_2$-$C_6$ alkenyl or $C_2$-$C_6$ alkynyl;

$R^4$, $R^5$, $R^6$ and $R^7$ are independently selected from H, $C_1$-$C_6$ alkyl, $C_2$-$C_6$ alkenyl, $C_2$-$C_6$ alkynyl; or $R^4$ and $R^7$ form together a —$CH_2$— linkage;

n is an integer selected from 1, 2, 3, 4, 5 or 6; and $PG^1$ is H or a protecting group selected from benzyl, t-butyl, THP, TMS or TBS.

2. The compound according to claim 1, wherein said compound is selected from:

(2S)—N-(benzyloxy)-2-{[4-(4-methoxyphenyl)piperazin-1-yl]carbonyl}-4-methyl pentan-1-amine ; or (2S)—N-(benzyloxy)-2-[(4-biphenyl-4-ylpiperazin-1-yl)carbonyl]-4-methylpentan-1-amine.

3. A N-hydroxyamide derivative selected from the group consisting of:

hydroxy((2S)-2-{[4-(4-methoxyphenyl)piperazin-1-yl]carbonyl}-4-methylpentyl)formamide: and {(2S)-2-[(4-biphenyl-4-ylpiperazin-1-yl)carbonyl]-4-methylpentyl}hydroxyformamide.

4. The N-hydroxyamide derivative according to claim 3, wherein said derivative is hydroxy((2S)-2-{[4-(4-methoxyphenyl)piperazin-1-yl]carbonyl}-4-methylpentyl) formamide.

5. The N-hydroxyamide derivative according to claim 3, wherein said derivative is {(2S)-2-[(4-biphenyl-4-ylpiperazin-1-yl)carbonyl]-4-methylpentyl}hydroxyformamide.

6. A method of treating arthritis, emphysema, multiple sclerosis or pre-term labor comprising the administration of a compound of Formula (I) to a subject having arthritis, emphysema, multiple sclerosis or pre-term labor,

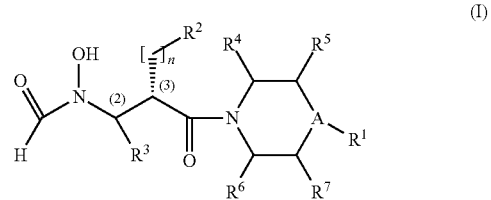

(I)

wherein:

A is N;

$R^1$ is selected from H, $C_1$-$C_6$ alkyl, $C_2$-$C_6$ alkenyl, $C_2$-$C_6$ alkynyl, $C_3$-$C_8$-cycloalkyl, heterocycloalkyl, aryl, heteroaryl, $C_3$-$C_8$-cycloalkyl $C_1$-$C_6$ alkyl, heterocycloalkyl $C_1$-$C_6$ alkyl, heteroaryl $C_1$-$C_6$ alkyl, amino or alkoxy;

$R^2$ is selected from H, $C_1$-$C_6$ alkyl, $C_2$-$C_6$ alkenyl, $C_2$-$C_6$ alkynyl, $C_3$-$C_8$-cycloalkyl, heterocycloalkyl, alkoxy, aryl or heteroaryl;

$R^3$ is selected from H, $C_1$-$C_6$ alkyl, $C_2$-$C_6$ alkenyl or $C_2$-$C_6$ alkynyl;

$R^4$, $R^5$, $R^6$ and $R^7$ are independently selected from H, $C_1$-$C_6$ alkyl, $C_2$-$C_6$ alkenyl, $C_2$-$C_6$ alkynyl; or $R^4$ and $R^7$ form together a —$CH_2$— linkage; and n is an integer selected from 1, 2, 3, 4, 5 or 6;

or pharmaceutically acceptable salts thereof, wherein carbons (2) and (3) are two chiral centers, chiral center (2) has a configuration selected from "S" and "R" and chiral center (3) has a "S" configuration.

7. The method according to claim 6, wherein said subject has multiple sclerosis.

8. The method according to claim 6, wherein said subject has arthritis.

9. The method according to claim 6, wherein said subject has emphysema.

10. The method according to claim 6, wherein $R^1$ is selected from aryl or heteroaryl.

11. The method according to claim 6, wherein $R^2$ is selected from H, $C_1$-$C_6$ alkyl, $C_2$-$C_6$ alkenyl or $C_2$-$C_6$ alkynyl.

12. The method according to claim 6, wherein $R^3$ is H.

13. The method according to claim 6, wherein $R^4$, $R^5$ and $R^7$ are H.

14. The method according to claim 6, wherein $R^1$ is selected from aryl or heteroaryl; $R^2$ is selected from H, $C_1$-$C_6$ alkyl, $C_2$-$C_6$ alkenyl, $C_2$-$C_6$ alkynyl, $C_3$-$C_8$-cycloalkyl, heterocycloalkyl or alkoxy; $R^3$, $R^4$, $R^5$ and $R^7$ are H; $R^6$ is selected from H or methyl; and n is an integer selected from 1, 2 or 3.

15. The method according to claim 6, wherein $R^2$ is selected from H, $C_2$-$C_6$ alkenyl, $C_2$-$C_6$ alkynyl, $C_3$-$C_8$-cycloalkyl, heterocycloalkyl or alkoxy.

16. The method according to claim 6, wherein said subject has pre-term labor.

17. The method according to claim 6, wherein said method comprises the administration of a compound according to Formula (I) in combination with pegylated or non-pegylated interferon beta, glatiramer, mitoxantrone, methotrexate, azathioprine, cyclophosphamide, methylprednisolone, prednisone, dexamethasone or cladribine to a patient having multiple sclerosis.

18. A pharmaceutical composition comprising at least one N-hydroxyamide derivative according to claim 3 and a pharmaceutically acceptable carrier, diluent or excipient.

19. A process for the preparation of a N-hydroxyamide derivative, comprising reacting a compound of Formula (II) with a formylating agent of formula (FA):

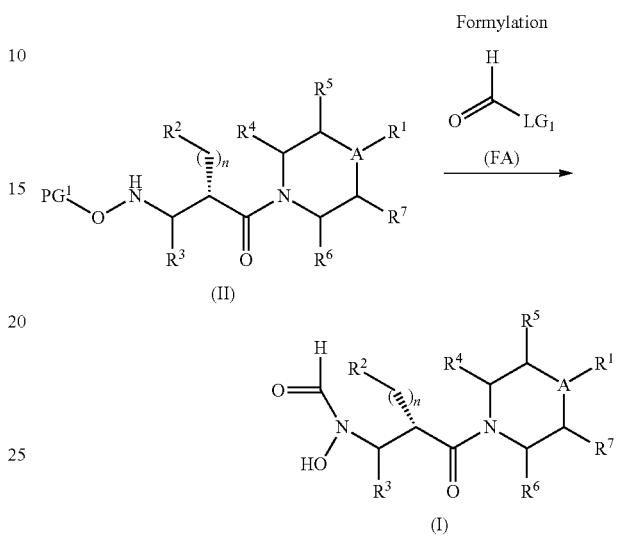

wherein:

A is N;

$R^1$ is selected from H, $C_1$-$C_6$ alkyl, $C_2$-$C_6$ alkenyl, $C_2$-$C_6$ alkynyl, $C_3$-$C_8$-cycloalkyl, heterocycloalkyl, aryl, heteroaryl, $C_3$-$C_8$-cycloalkyl $C_1$-$C_6$ alkyl, heterocycloalkyl $C_1$-$C_6$ alkyl, heteroaryl $C_1$-$C_6$ alkyl, amino or alkoxy;

$R^2$ is selected from H, $C_1$-$C_6$ alkyl, $C_2$-$C_6$ alkenyl, $C_2$-$C_6$ alkynyl, $C_3$-$C_8$-cycloalkyl, heterocycloalkyl, alkoxy, aryl or heteroaryl;

$R^3$ is selected from H, $C_1$-$C_6$ alkyl, $C_2$-$C_6$ alkenyl or $C_2$-$C_6$ alkynyl;

$R^4$, $R^5$, $R^6$ and $R^7$ are independently selected from H, $C_1$-$C_6$ alkyl, $C_2$-$C_6$ alkenyl, $C_2$-$C_6$ alkynyl; or $R^4$ and $R^7$ form together a —$CH_2$— linkage;

n is an integer selected from 1, 2, 3, 4, 5 or 6; and $PG^1$ is H or a protecting group selected from benzyl, t-butyl, THP, TMS or TBS; $LG_1$ is a leaving group selected from —OH, —OAc, —OPiv, —$OCH_2CN$, —$OCH_2CF_3$, —OPh or —OPfp.

* * * * *

UNITED STATES PATENT AND TRADEMARK OFFICE
CERTIFICATE OF CORRECTION

PATENT NO. : 7,998,964 B2
APPLICATION NO. : 12/094921
DATED : August 16, 2011
INVENTOR(S) : Dominique Swinnen et al.

It is certified that error appears in the above-identified patent and that said Letters Patent is hereby corrected as shown below:

Column 3,
Line 59, "term "MMPS" refers" should read --term "MMPs" refers--.

Column 4,
Line 39, "collagen X" should read --Collagen X--.

Column 5,
Lines 39-40, "Aryl include" should read --Aryl includes--.

Column 6,
Line 6, "to an aryl groups" should read --to aryl groups--.
Line 9, "to a $C_2$-$C_6$-alkenyl groups" should read --to $C_2$-$C_6$-alkenyl groups--.

Column 6,
Line 16, "Heteroaryl substituent" should read --heteroaryl substituent--.

Column 7,
Line 56, "or "$CC_1$-$C_6$-alkyl" or" should read --or "$C_1$-$C_6$-alkyl" or--.

Column 9,
Lines 40-41, "formed from to acid addition salts formed with" should read
      --formed from acid addition with--.

Column 10,
Line 11, "fibrob last" should read --fibroblast--.
Line 50, "dosage of about of 30μg" should read --dosage of about 30μg--.

Column 12,
Lines 5-6, "such as such as 3-phenyl" should read --such as 3-phenyl--.

Signed and Sealed this
Twenty-fourth Day of January, 2012

David J. Kappos
*Director of the United States Patent and Trademark Office*

Column 14,
Line 42, "such as such as 3-phenyl" should read --such as 3-phenyl--.

Column 15,
Line 2, "such as such as 3-phenyl" should read --such as 3-phenyl--.

Column 15,
Lines 32-33, "such as such as 3-phenyl" should read --such as 3-phenyl--.

Column 22,
Lines 18-19, "pathways for the will be described" should read
--pathways will be described--.

Column 31,
Line 55, "each as say" should read --each assay--.

Column 32,
Line 17, "NH2" should read --$NH_2$--.

Column 32,
Line 33, "NH2" should read --$NH_2$--.

Column 34,
Line 44, "Death are" should read --Deaths are--.